(12) United States Patent
Silver

(10) Patent No.: US 6,269,339 B1
(45) Date of Patent: Jul. 31, 2001

(54) SYSTEM AND METHOD FOR DEVELOPING AND SELECTING A CUSTOMIZED WELLNESS PLAN

(75) Inventor: Charles Silver, La Jolla, CA (US)

(73) Assignee: Real Age, Inc., San Diego, CA (US)

( * ) Notice: Subject to any disclaimer, the term of this patent is extended or adjusted under 35 U.S.C. 154(b) by 0 days.

(21) Appl. No.: 09/222,687

(22) Filed: Dec. 29, 1998

Related U.S. Application Data

(63) Continuation-in-part of application No. 08/833,145, filed on Apr. 4, 1997, now Pat. No. 5,937,387.

(51) Int. Cl.⁷ ............................................. G06F 17/60
(52) U.S. Cl. .............................. 705/2; 705/3; 600/300
(58) Field of Search ............................ 705/1, 2, 3, 4; 600/300, 301

(56) References Cited

U.S. PATENT DOCUMENTS

| | | | |
|---|---|---|---|
| 4,130,881 | 12/1978 | Haessler et al. | 364/900 |
| 4,872,122 | 10/1989 | Altschuler et al. | 364/554 |
| 5,000,188 | 3/1991 | Kojima | 128/687 |
| 5,025,374 | 6/1991 | Roizen et al. | 364/413.02 |
| 5,235,510 * | 8/1993 | Yamada et al. | 600/300 |
| 5,574,828 | 11/1996 | Hayward et al. | 395/50 |

FOREIGN PATENT DOCUMENTS

9513993 * 7/1995 (EP) .

OTHER PUBLICATIONS

Business wire, Wellness Checkpoint, pp. 1–3, Feb. 1993.*
Tecce Decarlo, et al, Health Literacy, pp 1, 1997.*
Bellamy David Scott, Individual Firm Demand for health and wellnes programs, pp 1, 1996.*
Moseti Harrison koroso, An in Depth analysis of the relationship between employee wellness programs and employee health care costs, pp 1 1996.*
Jerstad Sandra I, A needs analysis of a comprehensive wellness program, pp 1, 1994.*
Deakin Deborah, Employee wellness programs in public education k–12, pp 1, 1997.*
Jul. 1991 *Healthier People* (Version 4.0); Carter Center of Emory University; Health Risk Appraisal Program.
© 1995 *Healthier People—Health Risk Appraisal Report* (including sample report on fictional person, Susan A. Williams) [© by Risk Management Systems, Inc., Memphis, TN].
© 1994 *Nellcor© Healthquiz™ Prescreen™*(Preanesthetic Medical History Software, Version 2.1).

* cited by examiner

*Primary Examiner*—James P. Trammell
*Assistant Examiner*—Mussie Tesfamariam
(74) *Attorney, Agent, or Firm*—Roberts Aborkhair & Mardula

(57) ABSTRACT

The System and Method for Developing a Customized Wetness Plan of the present invention provides a means of measuring a user's wellness by determining a user's physiological age. The disclosed system and method also provides a means by which a user can learn about personalized wellness options, where the wellness options have been chosen for the user based upon wellness factors input by the user, additional constraints input by the user and the most recently available information relating to the health sciences. The user can select one or more of the disclosed options, and determine the potential effect implementing the options could have on the user's physiological age over the short or long term. In this fashion, the user can continue selecting various groups of alternatives until he or she has determined the group of options that the user would like to implement as a wellness plan. The user can then obtain further information regarding the chosen wellness plan from the system and method of the present invention. The disclosed system and method also provides a means whereby a user can monitor their progress toward improving wellness, wherein this progress can be positive or negative.

42 Claims, 31 Drawing Sheets

WELCOME, BOB    REAL AGE

DR. MICHAEL ROIZEN
CHAIRMAN, DEPT. OF
ANESTHESIA & CRITICAL CARE
UNIVERSITY OF CHICAGO
(PHOTOGRAPH)

OK

CLICK OK OR PRESS ENTER TO CONTINUE

FIGURE 2

| DO YOU USUALLY WEAR A SEATBELT? | (TESTING INFO.)<br>SERVER. RAMINGO<br>DB NAME: ALPHA TEST<br>USER. AAA0001075 |

● YES

● NO

☐ QUIT     PREVIOUS ◁❙  NEXT ❙▷

FIGURE 5

THINK ABUT A TYPICAL WEEK. HOW
OFTEN DO YOU EAT BREAKFAST?

(TESTING INFO.)
SERVER. RAMINGO
DB NAME: ALPHA TEST
USER. AAA0001075

● LESS THAN 1 TIME PER WEEK

● 1 TIME PER WEEK

● 2 TO 5 TIMES PER WEEK

● ALMOST EVERYDAY OR EVERYDAY

☐ QUIT                    PREVIOUS ◁◉     NEXT ◉▷

FIGURE 6

| Chronological Age | 10-year US Census Mortality Data[1] | Derived 10-year Survivability Data |
|---|---|---|
| 10 | 0.008 | 0.992 |
| 15 | 0.015 | 0.985 |
| 20 | 0.017 | 0.983 |
| 25 | 0.019 | 0.981 |
| 30 | 0.023 | 0.977 |
| 35 | 0.029 | 0.971 |
| 40 | 0.040 | 0.960 |
| 45 | 0.062 | 0.938 |
| 50 | 0.096 | 0.904 |
| 55 | 0.148 | 0.852 |
| 60 | 0.190 | 0.810 |
| 65 | 0.317 | 0.683 |
| 70 | 0.444 | 0.556 |
| 75 | 0.591 | 0.409 |
| 80 | 0.735 | 0.265 |
| 85 | 0.857 | 0.143 |
| 90 | 0.879 | 0.121 |

FIGURE 9

BASED UPON THE ANSWERS
YOU'VE PROVIDED, BOB

YOUR PHYSIOLOGICAL AGE IS
46.77

OK

CLICK OK TO ENTER THE PLANNER

FIGURE 15

Physiological Age: 46.77   Calendar Age: 46.90

Wellness Planner

| Select | Recommendations* | Maximum Age Reduction (years)** | Products |
|--------|------------------|--------------------------------|----------|
| ○— | Cigarette Smoking: Commit to stop smoking or if you already have keep up the good work. | 2.75 | —○ |
| ○— | Cholesterol and HDL: If cholesterol is high or your HDL is low reduce your dietary cholesterol, exercise and have 1 alcoholic drink a night. | 1.52 | —○ |
| ○— | Blood Pressure: Reduce your blood pressure to LESS than 120/80. | 1.24 | —○ |
| ○— | Stress: Learn methods to reduce your stress level and do them routinely. | 1.22 | —○ |
| ○— | Stamina: Do exercises that raise your heart rate to 70% of maximum ((220 minus your age) multiplied by 0.70) for 60 minutes per week. | 1.13 | —○ | with this plan: | Physiological Age | Calendar Age |
90 days from now:    46.77              47.15
3 years from now:    46.77              49.90

☐ Exit and Print                Previous ⇐    Next ⇒

*Consult your doctor before starting any Wellness plan. **Maximum age benefit in years younger if this were the only Wellness recommendation you did.

FIGURE 18

Physiological Age: 46.77 Calendar Age: 46.90

Wellness Planner

| Select | Recommendations* | Maximum Age Reduction (years)** | Products |
|---|---|---|---|
| ○— | Vitamin C: Take 250 mg (or the dietary equivalent) of Vitamin C, 3 times per day. | 0.64 | —○ |
| ○— | Folate: Take more than 670 micrograms (mcg) and up to 1 milligram (mg) per day. | 0.42 | —○ |
| ○— | Body Mass Index: Carefully begin a sustainable weight loss program. | 0.42 | —○ |
| ○— | Heart Rate: Increase your stamina activity. | 0.28 | —○ |
| ○— | Vitamin E: Take 400 I.U. per day of vitamin E. | 0.25 | —○ |

| with this plan: | Physiological Age | Calendar Age |
|---|---|---|
| 90 days from now: | 46.77 | 47.15 |
| 3 years from now: | 46.77 | 49.90 |

☐ Exit and Print         Previous ⇐      Next ⇒

* Consult your doctor before starting any Wellness plan. **Maximum age benefit in years younger if this were the only Wellness recommendation you did.

FIGURE 19

Physiological Age: 46.77  Calendar Age: 46.90

Wellness Planner

| Select | Recommendations* | Maximum Age Reduction (years)** | Products |
|---|---|---|---|
| ✓ | Cigarette Smoking: Commit to stop smoking or if you already have keep up the good work. | 2.75 | ○ |
| ✓ | Cholesterol and HDL: If cholesterol is high or your HDL is low reduce your dietary cholesterol, exercise and have 1 alcoholic drink a night. | 1.52 | ○ |
| ✓ | Blood Pressure: Reduce your blood pressure to LESS than 120/80. | 1.24 | ○ |
| ○ | Stress: Learn methods to reduce your stress level and do them routinely. | 1.22 | ○ |
| ○ | Stamina: Do exercises that raise your heart rate to 70% of maximum ((220 minus your age) multiplied by 0.70) for 60 minutes per week. | 1.13 | ○ |

| with this plan: | Physiological Age | Calendar Age |
|---|---|---|
| 90 days from now: | 43.49 | 47.15 |
| 3 years from now: | 40.04 | 49.90 |

☐ Exit and Print                    Previous ⇐    Next ⇒

*Consult your doctor before starting any Wellness plan. **Maximum age benefit in years younger if this were the only Wellness recommendation you did.

FIGURE 20

Physiological Age: 46.77 Calendar Age: 46.90

Wellness Planner

| Select | Recommendations* | Maximum Age Reduction (years)** | Products |
|---|---|---|---|
| ✓ | Vitamin C: Take 250 mg (or the dietary equivalent) of Vitamin C, 3 times per day. | 0.64 | ○ |
| ✓ | Folate: Take more than 670 micrograms (mcg) and up to 1 milligram (mg) per day. | 0.42 | ○ |
| ○ | Body Mass Index: Carefully begin a sustainable weight loss program. | 0.42 | ○ |
| ○ | Heart Rate: Increase your stamina activity. | 0.28 | ○ |
| ✓ | Vitamin E: Take 400 I.U. per day of vitamin E. | 0.25 | ○ | with this plan: | Physiological Age | Calendar Age
90 days from now: 43.49 47.15
3 years from now: 40.04 49.90

☐ Exit and Print          Previous ⇐     Next ⇒

*Consult your doctor before starting any Wellness plan. **Maximum age benefit in years younger if this were the only Wellness recommendation you did.

FIGURE 21

|  |  |  |
|---|---|---|
|  | Bob Barker's | Session Date 2/7/97 |
|  | Wellness Planner | Calendar 46.9 |
|  |  | Page: 1 |
| 5471 South Drexel Street | Physiological Age: | 46.8 |
| First Floor | With this Wellness Plan: |  |
| Chicago, IL, 60657 | 90 Day Target:[1] | 43.5 |
| This Location: | Long Term Target:[1] | 40.0 |

 You've chosen to follow 6 recommendations to help reduce your Physiological Age. Reach your 90 Day Target by following all selected recommendations for the next three months. Actions that have the biggest impact on your Wellness appear first.

| | Recommendation[2] | Maximum Physiological Age Reduction (years younger)[3] |
|---|---|---|
| 1. | Cigarette Smoking: Commit to stop smoking or if you already have keep up the good work. | 2.8 |
| 2. | Cholesterol and HDL: If cholesterol is high or your HDL is low reduce your dietary cholesterol, exercise and have 1 alcoholic drink a night. | 1.5 |
| 3. | Blood Pressure: Reduce your blood pressure to LESS than 120/80. | 1.2 |
| 4. | Vitamin C: Take 250 mg (or the dietary equivalent) of Vitamin C, 3 times per day. | 0.6 |
| 5. | Folate: Take more than 670 micrograms (mcg) and up to 1 milligram (mg) per day. | 0.4 |
| 6. | Vitamin E: Take 400 I.U. per day of vitamin E. | 0.3 |

[1] Plus time since date of this report.

[2] Consult your doctor before starting any age reduction strategy.

[3] Maximum age reduction benefit in years younger if this were the only age reduction strategy you did — Wellness strategies interact so combined benefit may be greater or less for you.

Questions or Comments?

FIGURE 22

Bob Barker's            Session Date:   2/7/97
Recommendation Details[1]      Calendar    46.9
                                                                                                  Page:          1

Listed below is additional information relating to the specific recommendations you've chosen to follow. Read all of these notes carefully before implementing any wellness recommendations.
Use the Personal Notes section to fill in the steps you're going to take to make your age reduction a reality.

Maximum Physiological Age Reduction (years younger):[2]     2.8

Cigarette Smoking: Commit to stop smoking or if you already have keep up the good work.
- Quitting cigarettes is tough. Your first time quitting smoking, you may only go a short distance. But like learning to ride a bike, you have to commit to getting back up and trying again.
- Increase exercise and water drinking; work with a group or a doctor.
- Smoking cessation is best achieved with nicotine replacement (gum or patch) and behavior modification.
- Fear of getting fat (obese) is one of the largest reasons people give for not quitting, but the fear of smoking should always be greater than the fear of fat. Most people over estimate the amount of weight gain that occurs after smoking cessation or don't gain weight at all. Even if a few pounds are gained in the process, it pales in comparison to the decrease in your RealAge from not smoking.
- Those who have stopped smoking will get more benefit from stopping the longer they don't smoke. If you have already stopped, keep up the good work. Remember, you are still benefitting from not smoking.
    *Personal Notes*_____

Maximum Physiological Age Reduction (years younger):[2]     1.5

Cholesterol and HDL: If cholesterol is high or your HDL is low reduce your dietary cholesterol, exercise and have 1 alcoholic drink per day.
TOTAL CHOLESTEROL:
- The first step to lowering cholesterol and retarding or reversing aging of your arteries and heart from cholesterol is to decrease the amount of saturated fat in your diet. Stopping smoking, regular exercise and 1 drink per day all have favorable effects on your cholesterol level.
- Those who need to worry the most about their cholesterol are those with other factors that age arteries and heart from cholesterol, i.e.) those whose mother or father died of a heart attack before the age of 55, smokers, diabetics and those with high blood pressure.
- Medications to lower cholesterol should only be taken after diet and lifestyle changes have not optimally succeeded. They are likely to be most helpful in people with more than one cause of aging of arteries are those who have already had a heart attack.

HDL:
- You should first consult with your physician to help you decide on the best treatment plan. In general, exercise, cessation of smoking and low cholesterol and low saturated fat diets are the best way to reduce your RealAge from this factor.
- Women who have passed menopause should consider estrogen replacement to decrease arterial age and reduce risk of heart disease (artherosclerosis). This should be done only with the advice of their physician.
- Some people may benefit from one alcoholic drink per night.
- Other medications are available to help reduce cholesterol or raise your HDL, but these should only be given by a doctor in select patients.
    *Personal Notes* _____

---

[1] Consult your doctor before starting any wellness strategy.

[2] Maximum Physiological Age Reduction benefit in years younger if this were the only wellness strategy you did — wellness strategies interact so combined benefit may be greater or less for you.

<div style="text-align:center">

Questions or Comments?
FIGURE 23

</div>

**Bob Barker's
Recommendation Details**[1]

Session Date: 2/7/97
Calendar 46.9
Page: 2

Listed below is additional information relating to the specific recommendations you've chosen to follow. Read all of these notes carefully before implementing any wellness recommendations.
Use the Personal Notes section to fill in the steps you're going to take to make your age reduction a reality.

Maximum Physiological Age Reduction (years younger):[2]    1.2

Blood Pressure: Reduce your blood pressure to LESS than 120/80.
- Know your blood pressure and reduce it with exercise, diet, stress reduction or medication to LESS than 120/80.
- Exercise: Exercising three times per week for 50 minutes can decrease SBP by 7mmHg and DBP by 5mmHG in 16 weeks resulting in a RealAge reduction of 2.1 Real Years.
- Salt Restriction: Reducing sodium intake from 400 to 1600 mg/day if you have salt-sensitive blood pressure reduces SBP 9 mmHg from age 25 to 55, or about 2.8 RealYears, on average.
- Weight Loss: If you have high blood pressure and are overweight, a comprehensive exercise and dietary plan is essential. Losing about 10% of your current weight can lead to a lower blood pressure. Losing and maintaining weight loss can also reduce cholesterol, reduce the incidence of arthritis and gallstones, and generally improve your quality of life.
- Decrease Excess Alcohol/Cigarette Consumption: Smoking cessation and reduction in alcohol consumption to no more than 1 drink per day can be an important part of blood pressure control.
- Stress Reduction: Adopting stress reduction methods, particularly exercise, can greatly decrease your RealAge.
- Take Antihypertensive Pills and Use Routinely: Drugs can treat and reduce abnormally high blood pressure. Complying with these regimens (taking the pills regularly) is important in retarding aging. If side affects bother you, talk to your doctor so pills that are less bothersome to you can be prescribed.
    *Personal Notes*_____

Maximum Physiological Age Reduction (years younger):[2]    0.6

Vitamin C: Take 250 mg (or the dietary equivalent) of Vitamin C, 3 times per day.
- There is absolutely no difference between natural and synthetic Vitamin C.
- Increase your consumption of fruits and vegetables to at least 5 servings per day. More is better, unless you use the blood thining medicine Coumadin or have a disease (hemochromatosis) with too much iron (Vitamin C increases iron absorption from the gut and intestines). You may also experience irritation of your stomach or bowels (see below - buffered calcium ascorbate).
- In addition, take Vitamin C supplements (250 or 500 mg three times per day (having more than 1500 mg per day isn't necessarily better). Keep in mind that popping vitamin tablets is not replacement for eating lots of fruits and vegetables. Make Vitamin C part of your daily routine.
- Do not use chewable Vitamin C tablets, as these may cause problems with your teeth. If you experience problems in your stomach because of Vitamin C, switch to buffered calcium ascorbate (not sodium ascorbate, as it contains too much sodium).
- Check with your physician if you have to take antibiotics (they may lose their effect in the urinary tract with Vitamin C), take Coumadin, use anti-depressant or anti-psychotic medication (Vitamin C increases their effects), have glucose or phosphate dehydrogenase deficiency, or have an iron storage desease (hemochromatosis).
    *Personal Notes* _____

Maximum Physiological Age Reduction (years younger):[2]    0.4

Folate: Take more than 670 micrograms (mcg) and up to 1 milligram (mg) per day.

---

[1] Consult your doctor before starting any wellness strategy.

[2] Maximum Physiological Age Reduction benefit in years younger if this were the only wellness strategy you did — wellness strategies interact so combined benefit may be greater or less for you.

Questions or Comments?
FIGURE 24

| | | |
|---|---|---|
| Bob Barker's | Session Date: | 2/7/97 |
| Recommendation Details[1] | Calendar Page: | 46.9 3 |

Listed below is additional information relating to the specific recommendations you've chosen to follow. Read all of these notes carefully before implementing any wellness recommendations.
Use the Personal Notes section to fill in the steps you're going to take to make your age reduction a reality.

- The U.S. recommended daily intake of 200 mcg for men and 180 mcg for women is not as beneficial as higher amounts of folate.
  - Largest food sources are orange juice (43 mcg/serving), white breads (6 mcg/serving), dried beans (84 mcg/serving), green salad (20 mcg/serving) and ready-to-eat breakfast cereals (100 mcg/serving on average).
  - Taking up to a 1000 mcg of folate is generally safe.
  - If you have kidney problems, you may need to take folate and reduce protein intake to control homocysteine levels.

*Personal Notes*_____

Maximum Physiological Age Reduction (years younger):[2]   0.3

Vitamin E: Take 400 I.U. per day of vitamin E.
- There is absolutely no difference between natural and synthetic Vitamin E. It is a safe drug, even 2000 IU's per day. It is not known to cause toxicity (see below).
- You are unlikely to get enough Vitamin E from food, so consider taking a supplement of 400 I.U. per day. Start immediately as it only makes arteries younger if they are not severely damaged.
- It reduces the aging of your arteries and there decreases heart disease and strokes in general; its ability to inhibit clots makes hemorrhagic strokes worse. If you are taking a blood thinner, consult a doctor before starting.
- Olestra binds Vitamin E; take 400 I.U. twice a day apart from meals if you consume Olestra.
- Vitamin E also reduces the rate of aging of the lungs.

*Personal Notes* _____

---

[1] Consult your doctor before starting any wellness strategy.

[2] Maximum Physiological Age Reduction benefit in years younger if this were the only wellness strategy you did — wellness strategies interact so combined benefit may be greater or less for you.

Questions or Comments?

FIGURE 25

RECOMMENDATION DESCRIPTION

- THERE IS ABSOLUTELY NO DIFFERENCE BETWEEN NATURAL AND SYNTHETIC VITAMIN C.
- INCREASE YOUR CONSUMPTION OF FRUITS AND VEGETABLES TO AT LEAST 5 SERVINGS PER DAY. MORE IS BETTER, UNLESS YOU USE THE BLOOD THINNING MEDICINE COUMADIN OR HAVE A DISEASE (HEMOCHROMATOSIS) WITH TOO MUCH IRON (VITAMIN C INCREASES IRON ABSORPTION FROM THE GUT AND INTESTINES). YOU MAY ALSO EXPERIENCE IRRITATION OF YOUR STOMACH OR BOWELS (SEE BELOW-BUFFERED CALCIUM ABSCORBATE).

PREVIOUS PAGE    NEXT PAGE 

OK

CLICK OK OR PRESS ENTER TO CONTINUE

FIGURE 26

RECOMMENDATION DESCRIPTION

- IN ADDITION, TAKE VITAMIN C SUPPLEMENTS (250 OR 500 mg) THREE TIMES PER DAY (HAVING MORE THAN 1500 mg PER DAY ISN'T NECESSARILY BETTER). KEEP IN MIND THAT POPPING VITAMIN TABLETS IS NOT REPLACEMENT FOR EATING LOTS OF FRUITS AND VEGETABLES. MAKE VITAMIN C PART OF YOUR DAILY ROUTINE.
- DO NOT USE CHEWABLE VITAMIN C TABLETS, AS THESE MAY CAUSE PROBLEMS WITH YOUR TEETH. IF YOU EXPERIENCE PROBLEMS IN YOUR STOMACH BECAUSE OF VITAMIN C,

PREVIOUS PAGE    NEXT PAGE 

OK

CLICK OK OR PRESS ENTER TO CONTINUE

FIGURE 27

RECOMMENDATION DESCRIPTION

PROBLEMS IN YOUR STOMACH BECAUSE OF VITAMIN C, SWITCH TO BUFFERED CALCIUM ASCORBATE (NOT SODIUM ASCORBATE, AS IT CONTAINS TOO MUCH SODIUM).
- CHECK WITH YOUR PHYSICIAN IF YOU HAVE TO TAKE ANTIBIOTICS (THEY MAY LOSE THEIR EFFECT IN THE URINARY TRACT WITH VITAMIN C), TAKE COUMADIN, USE ANTI-DEPRESSANT OR ANTI-PSYCHOTIC MEDICATION (VITAMIN C INCREASES THEIR EFFECTS), HAVE GLUCOSE OR PHOSPHATE DEHYDROGENASE DEFICIENCY, OR HAVE AN IRON STORAGE DISEASE (HEMOCHROMATOSIS).

PREVIOUS PAGE  NEXT PAGE 

OK

CLICK OK OR PRESS ENTER TO CONTINUE

FIGURE 28

RECOMMENDATION DESCRIPTION

ASCORBATE, AS IT CONTAINS TOO MUCH SODIUM).
- CHECK WITH YOUR PHYSICIAN IF YOU HAVE TO
TAKE ANTIBIOTICS (THEY MAY LOSE THEIR EFFECT
IN THE URINARY TRACT WITH VITAMIN C), TAKE
COUMADIN, USE ANTI-DEPRESSANT OR ANTI-
PSYCHOTIC MEDICATION (VITAMIN C INCREASES
THEIR EFFECTS), HAVE GLUCOSE OR PHOSPHATE
DEHYDROGENASE DEFICIENCY, OR HAVE AN IRON
STORAGE DISEASE (HEMOCHROMATOSIS).

PREVIOUS PAGE    NEXT PAGE 

OK

CLICK OK OR PRESS ENTER TO CONTINUE

FIGURE 29

SYSTEM AND METHOD FOR DEVELOPING AND SELECTING A CUSTOMIZED WELLNESS PLAN

RELATIONSHIP TO OTHER APPLICATIONS

This application is a continuation in part of Ser. No. 08/833,145, filed on Apr. 04, 1997 now U.S. Pat. No. 5,937,387.

FIELD OF THE INVENTION

This invention relates generally to a means for evaluating consequences of voluntary life style choices, habits, disease transitions, and genetic factors. In particular, this invention is a method and apparatus, that can (1) combine various health risk and health enhancing factors to determine a user's current physiological age; (2) interactively assist, motivate, and counsel the user in choosing health behavior interventions to move a user from a current relative risk level to a preferred lower level of risk; and (3) provide the user with a means of measuring his or her progress toward improved wellness.

BACKGROUND OF THE INVENTION

In at least partial response to the spiraling costs of health care, a renewed emphasis has been placed on preventive medicine and wellness. Wellness programs in increasing numbers are being offered by government and private entities. This emphasis has resulted not only in a need for a means of measuring and monitoring wellness, but also for ways to encourage and counsel individuals to adopt healthy behaviors.

While a tremendous amount of high quality medical evidence has been published, it is time consuming and costly to access this information and to review it on a regular basis. Even if an individual has access to specialized medical computer resources, it takes considerable knowledge, time, and effort to interpret the published medical findings. This difficulty is particularly the case where findings in one medical publication need to be interpreted in light of another publication, or are contrary to previously published findings.

In addition, if individuals want to improve their wellness level, it is not always readily clear what the options are and which one or more are best for a specific person in their specific situation. Even if an appropriate plan is chosen, without constructive feedback as to the results of one's efforts, it is difficult for that person to remain motivated.

Health risk assessments are being used with increasing frequency as a means to assess an individual's personal health habits and risk factors; estimate the individual's future risk of death, illness, or otherwise reduced quality of life; and provide counseling as to means of reducing this risk. Generally these assessments take the form of mortality risk estimates and counseling phrases based upon relative risk. An example of such a phrase is, "if you adhere to an exercise program as prescribed by your doctor, your relative risk of dying from heart disease over your lifetime will be 0.43 with a 95% confidence interval of 0.41–0.455, and you will extend your useful life expectancy by 0.1 years." Such a statement is too abstract and/or remote in time for most people to respond to it effectively. To tell someone that they may lower their risk of dying from a disease in the coming year from 0.00016 to 0.00014 per year has even less relevance. Similarly, risk may be assessed in either a percent or "one in one thousand" format. Again, this assessment does not provide the level of information needed for an individual to be properly motivated toward implementing healthier behaviors. Further, being advised of the probability as to when one may die at a period of time in the remote future has little relevance to a younger person.

Other health risk assessment programs provide the user with a written evaluation based upon their answers to a questionnaire. This evaluation may include a health risk age, a list of recommendations, and the health risk age that could apply if the user follows the recommendations for a specified period of time. In these programs the user has little or no input in determining the recommendations. Most individuals will not follow such a list of recommendations because they do not take into account the individual's inclinations. In addition, the user has no way of determining the relative physiological effect of each item within the list of recommendations; thus, if they do not wish to incorporate the entire list of recommendations, they do not have the information needed to make an informed decision as to which item(s) to include.

The following non-interactive medical systems are generally directed toward diagnostic purposes, and are for use by medical professionals. These systems do not provide motivational factors for a patient to change to a healthier life style.

U.S. Pat. No. 4,130,881 to Haessler et al. discloses a medical diagnostic tool for health care professionals comprising a means for automated medical history taking. Haessler discloses the use of automated logic, wherein the questions asked are dependent on the patient's responses to prior questions.

U.S. Pat. No. 4,872,122 to Autschuler et al. discloses an interactive statistical system and method for predicting expert decisions. In practice, this system analyzes several input responses, by utilizing statistical analysis and preprogrammed expert opinions, to determine a diagnosis.

U.S. Pat. No. 5,025,374 to Roizen et al. discloses a device which is used to record patient history. Answers to a set of medical questions are used by the device to select medical or it pre-operative tests.

U.S. Pat. No. 5,235,510 to Umata et al. discloses a picture archiving communication lot system that records and stores various digital image data. In use, a patient is examined by way of a medical imaging device. The image is digitized and thereafter stored in a database with other relevant patient attributes. At a later time, medical personnel retrieve the image and other attributes at a remote workstation.

A need exists for an interactive system that supplies users with an easily understandable measurement of their wellness, the know how to improve their wellness, a means of customizing a program for improving their wellness, and a means to monitor their progress to that end. This measurement and counseling must take place in a manner that motivates individuals to adopt healthy lifestyles without being so abstract that encouragement and monitoring are difficult. Such a system must be flexible, such that it can continue to be a useful tool for users as they change their lifestyle, proceed through their life cycle and have voluntary and involuntary life changes.

SUMMARY OF THE INVENTION

It is therefore an object of the present invention to provide a system that counsels individuals in a meaningful way to adopt and maintain healthy behaviors.

It is a further object of the present invention to provide a system that uses individual behaviors and factors in a forward chaining reasoning mode to provide wellness options from which a user can select a wellness plan, and to encourage user participation in the wellness plan by providing feedback relating to calculated physiological age.

It is a further object of the present invention to provide a system that can assist the individual in a backward chaining reasoning mode to determine the potential decrease in physiological age that could occur if the user were to implement a chosen wellness plan.

It is a further object of the present invention to provide a system for collecting information from user(s) related to factors that affect their wellness, and for counseling the user(s) on healthy behaviors.

It is a further object of the present invention to provide a system that considers interactions between and among health risk and health enhancing factors when determining their combined effect upon a user's physiological age.

It is yet a further object of the present invention to consider the effect that multiple factors relating to voluntary choices, habits, environment, disease transitions and genetic predispositions may have on the user's physiological age, and to provide counseling to the user to assist in changing such factors.

It is yet a further object of the present invention to allow for the assessment of the effects of such multiple wellness factors as accident prone behaviors, age of death of parents, air pollution, alcohol, allergies, angioplasty, aspirin, asthma, blood pressure, body mass index, breakfast, coronary artery bypass graft, calcium, cigarette smoking, diabetes, dietary cholesterol, dietary fiber, driving while intoxicated, eating between meals, education level of spouse, education status, employment status, estrogen, forced expiratory volume in one second, firearms, first myocardial infarction, folate, functional status, garlic powder, genetic makeup, genetic risks, green tea, HDL cholesterol, heart rate, helmet use, immunizations, income, iron, job strain, liver disease, low back pain, lycopene, major life events, marital status, meat eating, coronary artery disease, medication compliance, medication use, non-steroidal anti-inflammatory drug, occupation, parent's divorce, passive smoking exposure, pets, physical activities, renal disease, safety belt use, self reported health status, sleep, social contacts, stamina, strength, stress, stroke, suicide attempt, total cholesterol, traffic tickets, transfusions, vitamin A, B vitamins, vitamin C, vitamin D, vitamin E, white blood cell count, weight changes, zinc, and weight cycling, among others in the calculation of physiological age and counseling of users.

It is yet a further object of the present invention to be able to consider additional factors and to update those existing factors as documentation becomes available.

It is yet a further object of the present invention to provide decision nodes within the present invention, thereby allowing the user to automatically skip unnecessary questions and reduce the length of the session.

It It is yet a further object of the present invention to determine the composite relative risk associated with an individual's behavior through the use of a covariance model.

It is yet a further object of the present invention to provide an integrated user operated system for measuring a user's physiological age, presenting options to improve wellness based upon the user's wellness factors and self-imposed constraints, and calculating the potential effects of option combinations selected by the user.

It is yet a further object of the present invention to generate a list of the user's good, average and problematic health conditions and habits, including recommendations and encouragement concerning those behaviors.

It is yet a further object of the present invention to allow a user to interact with the system of the present invention so that the user can obtain feedback as to how changes to life style and health habits will affect the user's physiological age.

It is yet a further object of the present invention to provide a means whereby a user can determine the relative value of incorporating various wellness options.

It is yet a further object of the present invention to provide a means whereby a user can monitor the effects that varying combinations of choices would have on his or her physiological age, and then choose the desired combination of choices as his or her wellness program.

It is yet a further object of the present invention to assist the user in designing and implementing a wellness program based on individuals needs, circumstances, and preferences.

It is yet a further object of the present invention to recommend various kinds of resources to aid the user in carrying out the course of action decided upon.

It is yet a further object of the present invention to furnish a list of questions that the user should ask his or her doctor as he or she progresses in the personalized wellness program.

It is yet a further object of the present invention to provide a means for maintaining current and accurate information about the user, and to use that updated information to recalculate physiological age, to encourage the user to continue participation in a wellness program and to provided updated options for healthy actions to be taken by the user.

It is yet a further object of the present invention to detect and record changes in the user's physiological age over time and to provide guidance to the user regarding any changes and their impact thereon.

It is yet a further object of the present invention to graphically compare the user's current physiological age to both the user's previous physiological age results and the user's chronological age group at each time they complete the input portion of the present invention.

It is yet a further object of the present invention to output educational materials related to user selected wellness factors.

These and other objectives and advantages of the present invention will be apparent to those of ordinary skill in the art upon review of the following disclosure.

The present invention is an interactive wellness system that uses a means for collecting information relating to a user's voluntary choices, habits, environment, disease transitions and genetic predispositions; a means for consistently measuring a user's wellness by determining his or her physiological age; a means for presenting the user with expert knowledge, know-how, and resources to improve his or her wellness, including presenting the user with wellness options; a means for allowing a user to determine the effects varying combinations of wellness options could have on his or her physiological age; a means for allowing the user to choose the combination of wellness options that he or she wishes to follow; a means for monitoring a user's progress toward improving wellness by measuring physiological age and a means for incorporating new medical data and new user data into the system.

It is further contemplated that the present invention is suitable for use in any situation in which a person's current state of wellness can be graded. Exemplary uses include insurance, corporate wellness programs, health care facilities, pre- and post-surgical facilities, sports and health clubs, weight management programs, smoke cessation programs, and preventive care programs.

In the insurance industry, health and life insurance premiums are calculated based on the applicant's age, sex, and habits such as smoking. Insurance concerns sometimes administer a questionnaire to collect data about pre-existing health conditions. The insurer can use this data to deny applicants coverage for some conditions. The system of the present invention supplies new statistics for calculating health and life insurance premiums. It collects information about exercise, diet, habits, health history and conditions, as well as other factors. The present invention uses this data to calculate the users' current wellness state, which can be used to stratify a pool of insurance applicants and policyholders according to degree of wellness. Insurance is, enterprises can use this stratification level data to calculate premiums based on wellness. As a result, applicants who maintain a higher state of wellness relative to other same age and gender applicants can receive lower premiums. Applicants with a lower wellness status can receive a reward (such as a reduced premium) for improving their state of wellness. The system of the present invention can process a large amount of input data and logic to calculate the users correct wellness stratification level, which is useful in this situation.

Corporate wellness programs support a range of volunteer activities to improve employee wellness, such as fitness centers, diet and nutrition classes, smoke cessation programs, screening interventions, and health education classes. While some wellness programs provide screening and counseling to help employees select appropriate activities, in the general case employees decide which activities they want to engage in without such screening and/or counseling.

The present invention complements either of these infrastructures by assisting the user in choosing exercise, diet, habit(s), and other types of wellness activities. The present invention stratifies users into graded levels of health using a substantial range of wellness factors. The system then evaluates this stratification data and compares it to curves of similar factors for specific age groups. The curves which are closest to the calculated factors for the individual are a meaningful measurement of the equivalent physiological age of the individual. The present invention also allows the user to input additional constraints to be used by the system in suggesting appropriate wellness activities. The user then considers varying combinations of recommended activities and chooses their desired wellness program. The system then provides choices available for improving physiological age, wherein these choices are specifically tailored to the individual user.

A sampling of the health care facilities that must collect a large amount of patient wellness data prior to making wellness recommendations includes primary care, preventive health nutrition, and geriatric. Physicians must review a great deal of high quality medical literature in conjunction with a patient's given data to recommend appropriate courses of action to maintain or improve the patient's condition. On a case-by-case basis, this data collection task is difficult and time-consuming. In the context of current trends to reduce costs, most physicians cannot afford to spend a lot of time collecting and reviewing data. Various guidelines offer an alternative solution. However, physicians still must collect a large amount of up-front data concerning a patient. Moreover, recently published guidelines are becoming more complex, requiring even more time to select guidelines which fit the patient's condition. The wellness measurement and wellness options systems of the present invention collect data directly from the patient. The physician can augment this data with test results pertaining to the patient, such as a patient's blood pressure, by using the system's input means. The wellness option(s) system then analyzes patient data according to guidelines to determine suitable courses of action.

Wellness measuring, wellness options, and wellness monitoring could also be used in the pre- and post-surgery facilities. Anesthesiologists and surgeons are rarely trained in the field of prevention. These systems can serve as an adjunct tool. For example, surgeons or anesthesiologists could show surgery patients, such as individuals undergoing arterial reconstruction, the effect of smoking on their physiological age—a powerful motivator at this critical period in a person's life. The wellness option(s) system could offer various courses of action to elevate the patient's state of wellness. The monitoring system could be used by the patient's primary care practice to track the patient's progress toward reaching an improved level of wellness.

The monitoring system of the present invention can be used in any situation where it is valuable to measure a person's progress toward reaching a different wellness state. For example, if the user decides to carry out a personal weight loss program, the user could record his or her weight over the weight loss period and chart progress made toward the weight loss goal. The monitoring system can collect the performance data, determine any changes in data, interact with the wellness system and report the results as a physiologic age change. The wellness measurement, suggested options, choice and monitoring systems of the present invention provide the means to meet the requirements of any situation requiring a measurement of wellness, user-specific recommendations, realistic and individually tailored user goals, and a technique to measure user progress toward reaching such goals.

The perception of success of most wellness activities is largely shaped by individual expectations and feelings. The interaction of the monitoring and measuring systems of the present invention provides a physiologic age measurement that can be used to calculate a single measurement of physiological age for a variety of wellness activities, thereby measuring the to value of these activities. The measuring and recommendation systems interact to generate specific wellness options for the user, which often will increase the user's motivation to change behavior resulting in improved wellness. This measurement allows for setting specific wellness goals and measuring progress toward those goals, thereby providing motivation for the user to continue the program.

Once a person elects to carry out a wellness program, the system then interacts with the user to set short and long-term wellness goals. The present invention can elicit information about resource constraints to help users plan realistic wellness goals. Unlike general recommendations found in consumer books, magazines, or pamphlets, the present invention can make specific recommendations based on the user's state of wellness, and can also show how any set of combinations chosen by the user will affect his or her state of wellness.

For the sake of simplicity, the systems of the present invention will be illustrated using a personal wellness program as an example situation. The present invention is not limited to this particular embodiment, as it is contemplated that the systems of the present invention can be used in a wide range of other situations.

BRIEF DESCRIPTION OF THE DRAWINGS

FIG. 2 depicts the opening page of the opening interface.

FIG. 5 shows an example of a Personal Profile window.

FIG. 6 shows an example of a Personal Profile window.

FIG. 9 depicts an absolute survival data set.

FIG. 15 depicts an example of a window informing the user of his or her physiological age.

FIG. 18 shows an example of an age reduction plan window, without selected plan items.

FIG. 19 shows an example of an age reduction plan window, without selected plan items.

FIG. 20 shows an example of an age reduction plan window, with selected plan items.

FIG. 21 shows an example of an age reduction plan window, with selected plan items.

FIG. 22 shows an example of a plan report.

FIG. 23 shows an example of a plan report.

FIG. 24 shows an example of a plan report.

FIG. 25 shows an example of a plan report.

FIG. 26 shows an example of an educator window.

FIG. 27 shows an example of an educator window.

FIG. 28 shows an example of an educator window.

FIG. 29 shows an example of an educator window.

DETAILED DESCRIPTION

The system of the present invention includes a data processing means such as a client computer system that communicates with a server computer system. The client computer system can be of any type using any type of operating system. In a preferred embodiment, the client computer system is an IBM or IBM compatible type computer using an Intel 80-series or Pentium chip, and running an operating system such as Microsoft Windows. Also in this preferred embodiment, the server computer system uses an operating system such as Microsoft Windows NT. An alternative embodiment is a client computer system based on an Intel 80-series Pentium or Pentium Pro microprocessor, running Microsoft Windows 95, and a server computer system based on an Intel Pentium or Pentium Pro microprocessor, running Windows NT. In a preferred embodiment, the client computer system and server computer system communicate using NetBIOS protocol. The use of this system as an example is not meant to limit the present invention to such a processing means, as it is contemplated that the present invention is suitable for use with any standard computer, and a person of ordinary skill in the art can determine many other data processing systems suitable for use with the system of the present invention. Furthermore, additional embodiments of the present invention can be accessed through either an internet or intranet format or the present invention could easily be implemented in a stand alone workstation or PC.

The processing means includes an input means, such as a keyboard, mouse, pen pointer, touch screen, microphone, trackball, joystick and/or other input means known in the art and used to input information to a computer. The processing means also includes a presentation means for presenting the output data to a user, such as a display monitor, television, printer, and/or other visual output means; and an output means for producing voice, music, or other sound output to the user. The processing means further includes enough memory, connected to the input means, to store at least any input data accepted by the system. The system also comprises memory for storing and running instructions regarding the covariance model calculations of the present invention. The processing means also has a logic means sufficient to manipulate data and run the application. The logic means can be a microprocessor or other micro controller with memory. The logic means is connected to the input means and presentation means. The processing means can also include a hand-held processing means, particularly for use in running the client application. The hand-held processing means could include both input means and presentation means.

Figure 1:
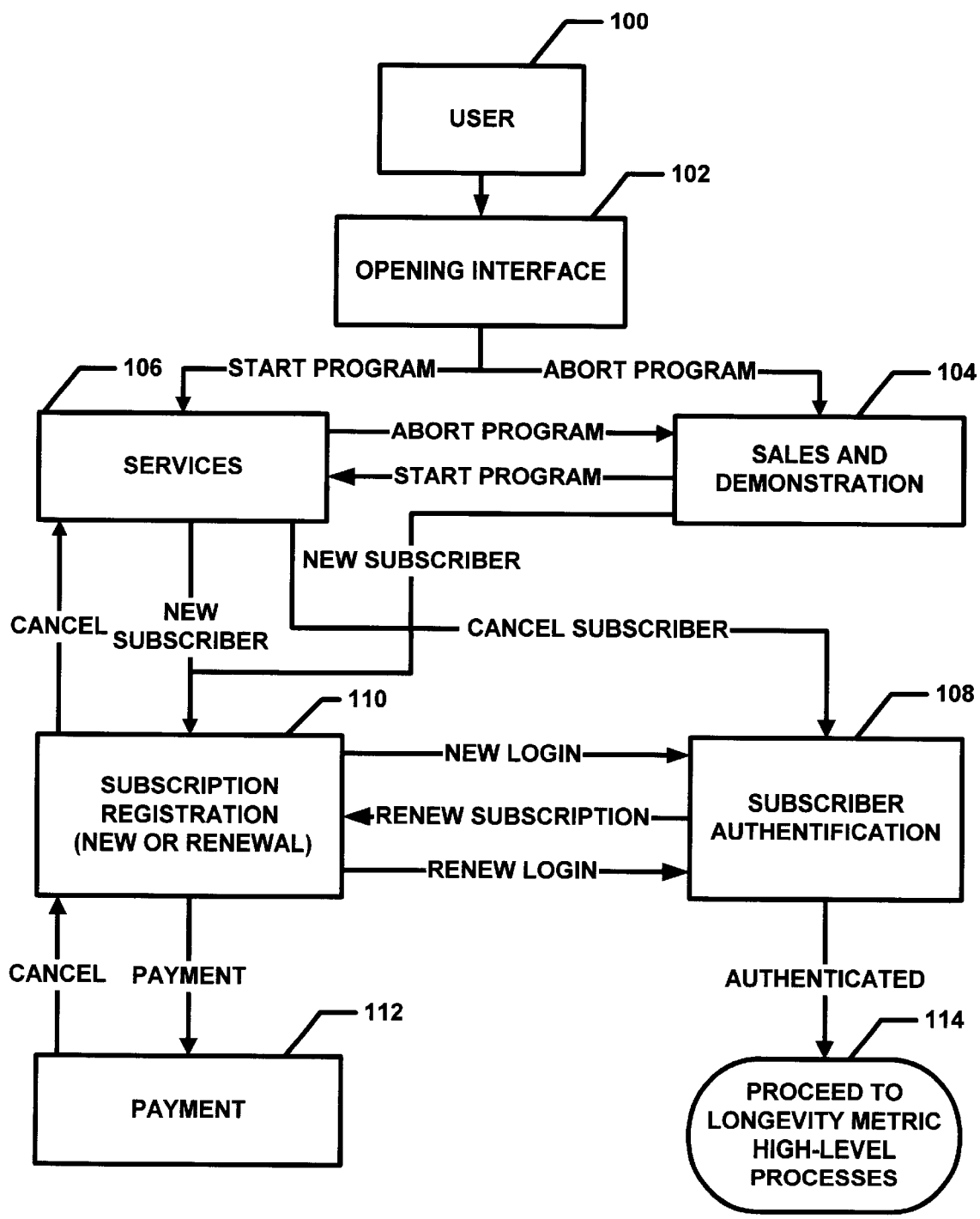
FIG. 1 sets forth the opening interface processes of the present invention.

FIG. 1 sets forth the opening interface processes of the present invention. Upon accessing the present invention, the user is presented with opening interface 102. At this point, the user can choose whether to learn more about the program through sales and demonstration 104, or begin the program 106. If the user is a current subscriber, the subscription is authenticated 108. If the user is not a current subscriber, the user is registered by initiating or renewing subscription 110, and payment is processed 112. After completion of subscription authentication 108 or subscription registration 110, the program proceeds to longevity metric high-level processes.

FIG. 2 depicts an opening page window of opening interface 102.

Figure 3:
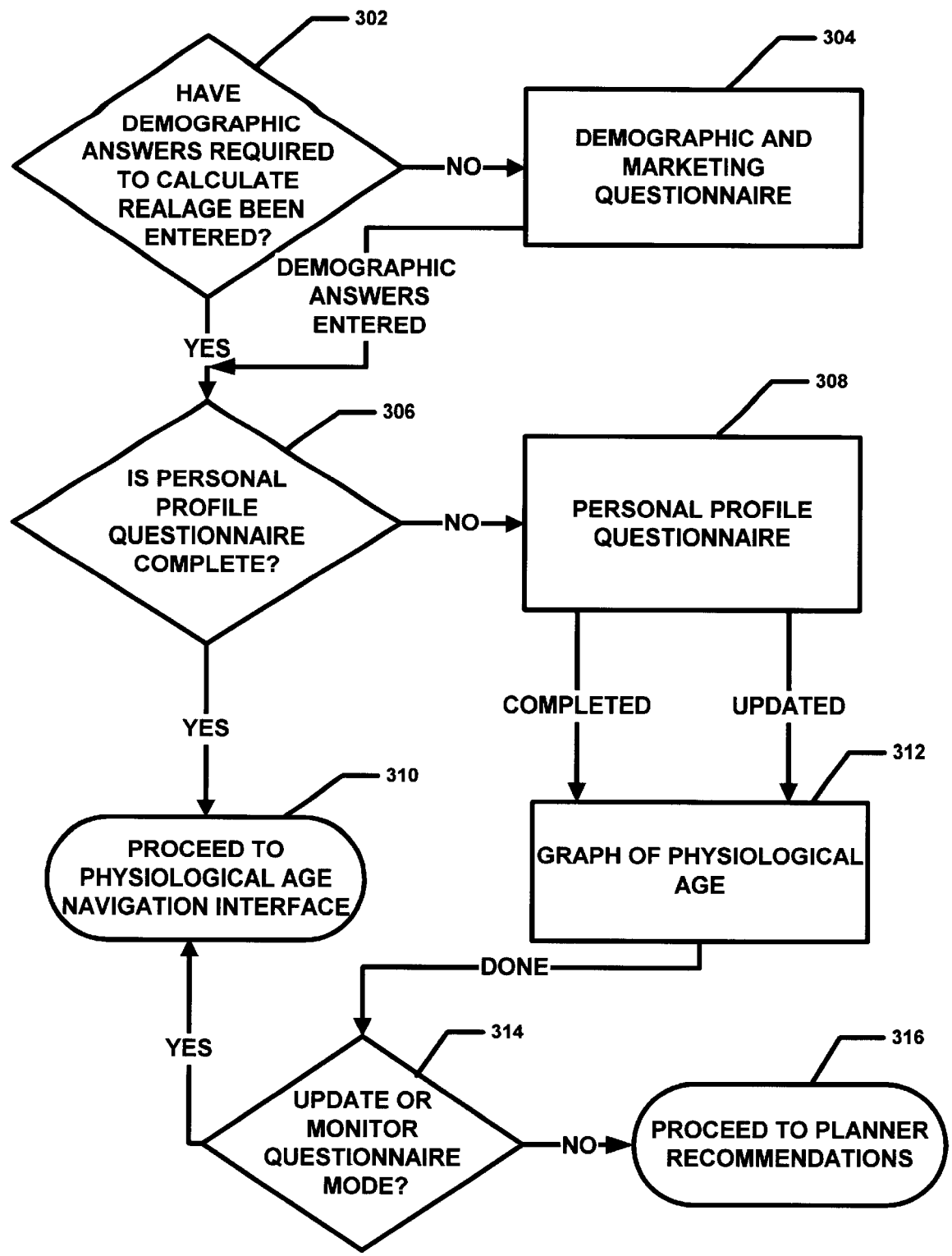
FIG. 3 sets forth the physiological age calculation overview.

FIG. 3 sets forth the physiological age calculation overview of the present invention. The system first determines whether demographic and marketing information has been entered by the user 302. If this information has not been entered, an optional demographic and marketing questionnaire is administered 304. Once demographic and marketing information has been entered or bypassed, the system determines whether the personal profile is complete 306.

Personal profile characteristics include age, life style, habit/environment, medical and genetic information about a user. Personal profile characteristics are used to stratify a user into a correct relative probability group, personalize recommendations and educators, and provide information to system and business functions. In cases where the user knows the answer to a personal profile characteristic, he or she can directly enter the information. In some cases where a user does not know the answer to a personal profile characteristic, the user can answer a series of questions related to the personal profile characteristic in question, and the answer can be derived by the system; that is, the system can manipulate the input data into transformed data. For example, while the user might not know the number of kilocalories expended each week during exercise, by inputting the frequency, duration and intensity of the physical activities, the system can then determine the kilocalories expended using techniques known in the art. Personal profile characteristic business processes then perform operations on the user's answers to determine a personal profile characteristic value. Some business processes supported by personal profile characteristics are as follows: the personal profile characteristic can perform a calculation on user-entered numerical answers to derive a personal profile characteristic value; or the personal profile characteristic can evaluate user-entered data against conditional rules which point to an associated value. After the rules have been evaluated, the personal profile characteristic summarizes the values for each true rule into a composite score.

The personal profile questionnaire includes a health profile questionnaire. The health profile questionnaire is designed to review a large volume of information related to personal profile characteristics. It employs decision nodes to automatically skip unnecessary questions and to reduce the length of the session. After the user answers a question, the present invention evaluates a series of conditional rule(s) to select the next appropriate question. These rules are capable of evaluating the user's current answer, previous answers, demographic data, and the current time/date. For example, if the user is male, pregnancy questions are skipped.

On subsequent uses, the health profile questionnaire is used to collect performance data related to the combination of recommendations that the user has chosen to adopt as their wellness plan. To update information about factors not associated with a current plan, the user can select and enter information about them at any time.

The health profile questionnaire is used to assess a user's relative wellness for a set of relative risk factors. Each factor is associated with a series of relative probabilities that a particular person will live for a period of time. Information from the health profile questionnaire is then used to determine the user's relative risk stratification level. The relative risk factors can relate to voluntary life style choices, habit, environment, disease transitions or genetic predispositions. Examples of factors include: accident prone behaviors, age of death of parents, air pollution, alcohol, allergies, angioplasty, aspirin, asthma, blood pressure, body mass index, breakfast, coronary artery bypass graph, calcium, cigarette smoking, diabetes, dietary cholesterol, dietary fiber, driving while intoxicated, eating between meals, education level of spouse, education status, employment status, estrogen, forced expiratory volume in one second, firearms, first myocardial infarction, folate, functional status, garlic powder, genetic makeup, genetic risks, green tea, HDL cholesterol, heart rate, helmet use, immunizations, income, iron, job strain, liver disease, low back pain, lycopene, major life events, marital status, meat eating, coronary artery disease, medication compliance, medication use, non-steroidal anti-inflammatory drugs, occupation, parent's divorce, passive smoking exposure, pets, physical activities, renal disease, safety belt use, self reported health status, sleep, social contacts, stamina, strength, stress, stroke, suicide attempt, total cholesterol, traffic tickets, transfusions, vitamin A, B vitamins, vitamin C, vitamin D, vitamin E, white blood cell count, weight changes, zinc, and weight cycling, among others.

Relative risk is the ratio of the occurrence of death in people with an attribute to the incidence in people without an attribute. Relative risk does not provide information about the magnitude of absolute risk; that is, how many people have the attribute and therefore are at risk of death. For example, even if the relative risk is large, the size of the absolute risk of death is small if the attribute is rare. Relative risk does convey information about the strength of the association between the attribute and mortality. Assuming 1.00 as the baseline, the higher the deviation of the relative risk from the baseline, the more the attribute is a cause (or marker) of mortality. Conversely, the lower the deviation, the less the attribute is a cause (or marker) of mortality. Attributes with relative risks above the baseline are considered causes (or markers) of mortality. Attributes with relative risks less than 1.00 are treated as beneficial. For example: the mortality rate from lung cancer in cigarette smokers is 0.96 per 1,000 people/year, while the mortality rate from lung cancer in nonsmokers is 0.07 per 1,000 people/year. The relative risk is equal to 0.96 divided by 0.07, which is 13.7. Thus, a smoker is 13.7 times more likely to die in the next ten years than is a non-smoker.

The medical and health literature widely report their results in terms of relative risk. For example, the mean of vitamin C supplement use is 140 mg/day. Where the supplemental use of vitamin C is in the range of 1–159, the relative risk is 1.00; where the supplemental use of vitamin C is in the range of 160–599 the relative risk is 0.93; and where the supplemental use of vitamin C is in the range of 600 or more, the relative risk is 0.90.

In a minority of studies, the baseline group is not defined as the mean group. In the prior example, the baseline group is defined as the mean since the mean 140 mg/day is in the range 0 to 159 mg/day. Some studies contrast the optimal and worst populations to show a higher effect than if the optimal and mean populations were compared. Other studies use other baselines. The use of baselines other than the mean is a barrier when adjusting the mortality index (assumed to be the mean) by a mortality effect of an attribute which does not use the mean as a standard. Therefore, in the preferred embodiment, relative risks are re-calibrated using the mean population.

Some studies define discrete populations. Using the example above as an illustration, the study authors may have defined the populations as 0, 160 and 600. Therefore, a user's answer of 140 would lie between the first and second populations. In these kinds of cases, the population definitions are broadened to accommodate answers which lie between populations. In the preferred embodiment, discrete populations are redefined as the range (population$_{(n)}$, population$_{(n+1)}$). Thus, the populations of the above example become 0–159, 160–599 and 600 or more.

Stratification rules are the mechanism used to determine which group and associated relative risk, fits the person's characteristics. Stratification rules use personal profile characteristic information which is calculated from the health profile questionnaire process. The associated stratification rules are processed to determine the correct relative risk classification. Where the question corresponding to the wellness factor is irrelevant the risk classification is set to 1.00. Where the response to the question corresponding to the wellness factor is uncertain the risk classification is set to the median or other predetermined level. Where the question corresponding to the wellness factor is not answered the risk classification is set to 1.00. Thus, test results are not invalidated where the user is unwilling or unable to answer every relevant question set forth in the health profile questionnaire. Table One sets forth examples of wellness factor scale information arrays.

TABLE 1

| Wellness Factor | Age | Optimal | Optimal Name | Average | Average Name | Worst | Worst Name |
|---|---|---|---|---|---|---|---|
| Vitamin C | 45.00 | 44.00 | 600 mg/day | 46.00 | 140 mg/day | 47.00 | ≦35 mg/day |
| LDL Cholesterol | 45.00 | 42.00 | <178 mg/dl | 45.00 | 229 mg/dl | 47.00 | >244 mg/dl |
| Energy Expenditure | 45.00 | 41.00 | 3500 kcals/day | 44.00 | 500–2000 Kcals/day | 46.00 | <500 kcals/day |
| Stop Smoking | 45.00 | 33.00 | Non-smoker | 45.00 | Undefined | 45.00 | >2 packs/day |
| Body Mass Index | 45.00 | 40.00 | 20 to 22.99 | 41.00 | 23 | 46.00 | >36 |

A composite survival probability, which is the product of all survival probabilities and an adjustment for covariance among the factors, is then calculated and used to adjust the average survival probability rate. The result is a survival probability rate adjusted for the user's level of wellness (users' survival probability rate.) This user-specific probability rate is then compared to the average survival probability rate of individuals of the same gender to determine the physiological age. Thus, the physiological age is equal to the chronologic age at which the user's survival probability rate equals the average survival probability rate of an individual of the same gender. Stated in another way, a user's physiological age is equal to the calendar age of an average person of the same gender with a comparable risk stratification level. Thus, a user's physiological age is a metric; that is, it is a meaningful number used to measure wellness.

Figure 4:
FIG. 4 shows an example of a Personal Profile window.

If the personal profile questionnaire is not complete, the personal profile questionnaire is administered 308. FIGS. 4, 5 and 6 depict examples of personal profile questionnaire windows. If the personal profile questionnaire was complete, the system proceeds to physiological age navigation interface 310.

Upon completing or updating the personal profile questionnaire, a graph depicting the user's physiological age is presented to the user 312. If the user wishes to update or monitor the questionnaire mode 314, the system proceeds to physiological age navigation interface 310. If the user does not wish to update or monitor the questionnaire mode 314, the system proceeds to planner recommendations 316.

Figure 7:
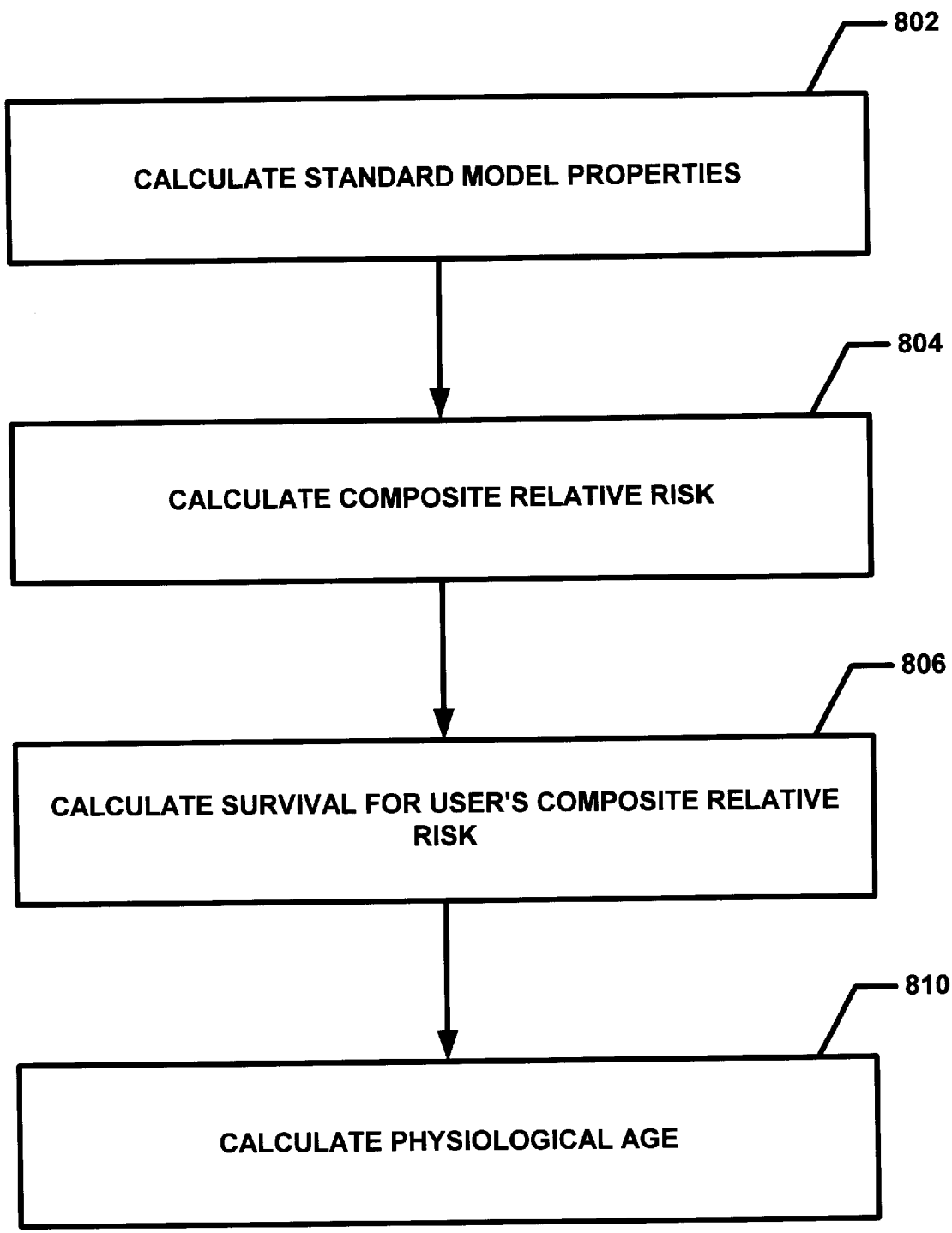
FIG. 7 sets forth the steps required to determine an individual's physiological age.

FIG. 7 sets forth the steps required to determine an individual's physiological age. This requires calculating standard model properties 802, calculating composite relative risk 804, calculating survival for the user's composite relative risk 806, and calculating the user's physiological age 808.

Figure 8:
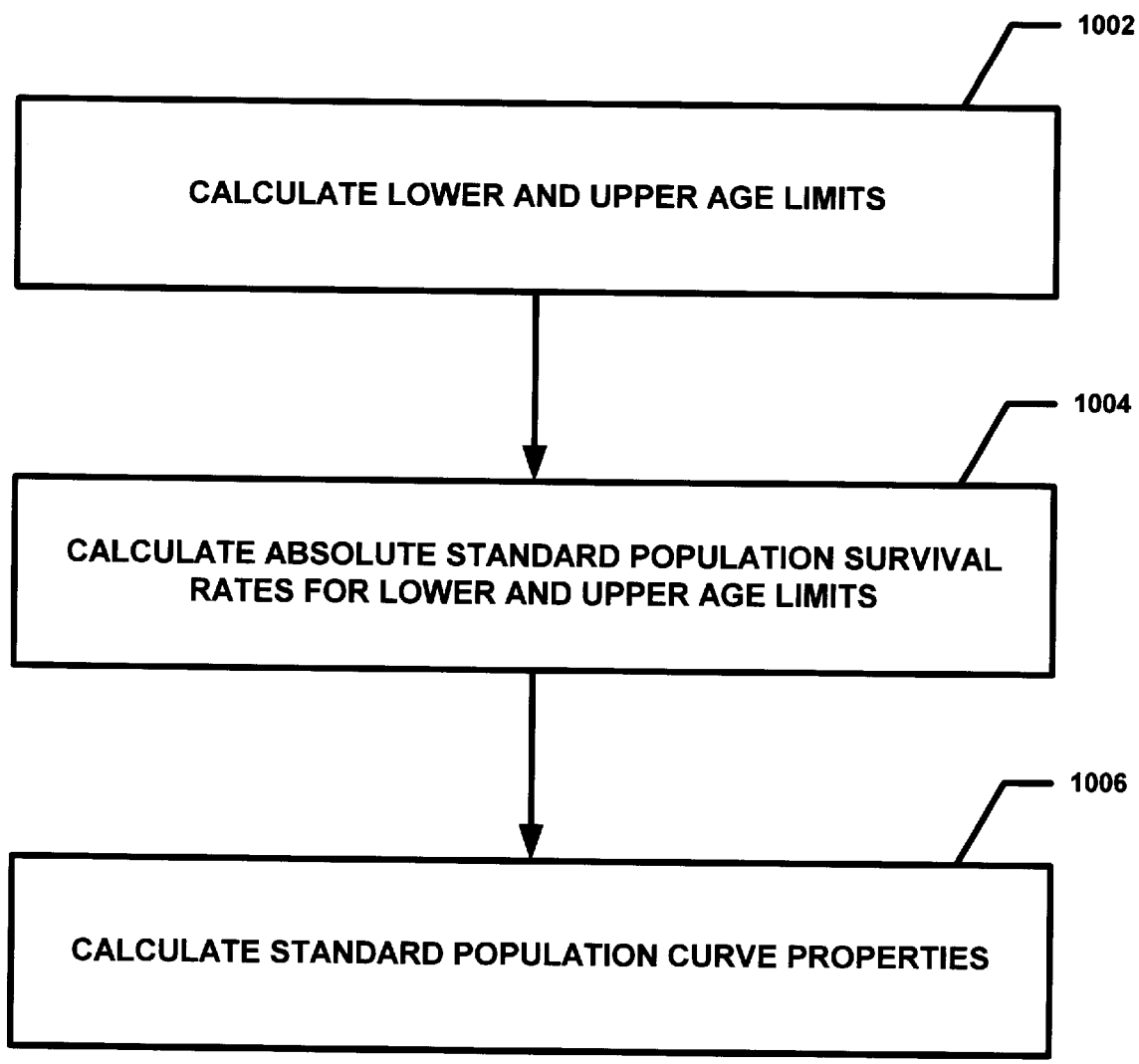
FIG. 8 sets forth the standard model properties that must be calculated in determining a user's physiological age.

FIG. 8 sets forth the standard model properties that must be calculated to determine a user's physiological age. This includes calculating lower and upper age limits 1002, calculating absolute standard population survival rates for lower and upper age limits 1004, and calculating the standard population curve properties 1006. The lower age limit (LAL) is equal to the chronological age minus fifteen, where the LAL range is equal to [5,80]. The upper age limit (UAL) is equal to the chronological age plus fifteen, where the UAL upper range is equal to [90].

The absolute survival rate conveys the probability that a person will live for a period of time. The survival proportion explains the relationship between survival-mortality probabilities. If survival varies, the constant value tells how much mortality should change. To determine the physiological age, one must first generate the absolute survival data set for a standard population, generate the absolute mortality data set, determine the absolute survival proportion curve parameters for each relative risk population, generate the final survival curve model points (attribute) from beta1 to beta0, and then calculate the physiological age.

The absolute standard population survival rate for lower age limit ($ASR_{SL}$) thus equals: US Census Table times (Survival Rate for AGE=LAL). The absolute standard population survival rate for upper age limit ($ASR_{UL}$) thus equals: US Census Table times (Survival Rate for AGE=UAL).

The absolute survival data set for a standard population is generated by subtracting the absolute mortality rate from one, and repeating this process for each chronological age group until data is generated for all groups. In a preferred embodiment, the ten year U.S. Census mortality data is used. The absolute mortality rate is equal to the mortality risk at a given age. FIG. 9 depicts an absolute survival data set based upon U.S. Census data published in July 1991.

The absolute mortality data set (attribute) is determined by generating absolute mortality rate (attribute) data points for each five-year increment from 10 to 90. The absolute mortality rate (attribute) is equal to (one minus the stratified relative risk classification for the attribute) times (one minus the absolute mortality rate standard for a given 5 year age group).

The absolute survival proportion curve parameters are determined for each relative risk population by calculating the one year survival proportion change rate, (Beta1) and the base attribute (Beta0). The survival proportion change rate is determined by calculating the lower and upper survival portion. The lower survival portion is equal to the absolute survival rate at the lower limit age divided by the absolute mortality rate at the lower limit age, wherein the lower limit age is 20. Upper survival proportion is equal to the absolute survival rate at the upper limit age divided by the absolute mortality rate at the upper limit age, wherein the upper limit age is 90. The survival proportion difference is then determined by calculating the distance between the two points; that is, the lower survival proportion minus the upper survival proportion. The one year survival proportion change rate is thus the survival proportion difference divided by the difference between the upper limit age and the lower limit age.

The base attribute, (Beta0) is needed to determine the correct survival proportion value when age and Beta1 are multiplied. The base attribute is equal to the lower survival proportion minus the lower limit age survival proportion value. The lower limit age survival proportion value is determined by multiplying the lower limit age by the one year survival proportion change rate.

The final survival curve model points (attribute) from Beta1 and Beta0 natural log equations are generated by determining the survival proportion unadjusted, which is equal to Beta1 times the current chronological age; determining the survival proportion value adjusted, which is equal to Beta0 plus the survival proportion unadjusted; determining the non-linear survival value proportion adjusted value, which is equal to the exponential of the survival proportion adjusted; and determining the absolute survival rate, which is equal to the nonlinear survival value proportion adjusted value divided by the sum of the nonlinear survival value proportion adjusted value plus one. This process is repeated until survival rate data has been generated for all five year increments. The true and natural log formula derived absolute survival rates are then correlated.

Figure 10:
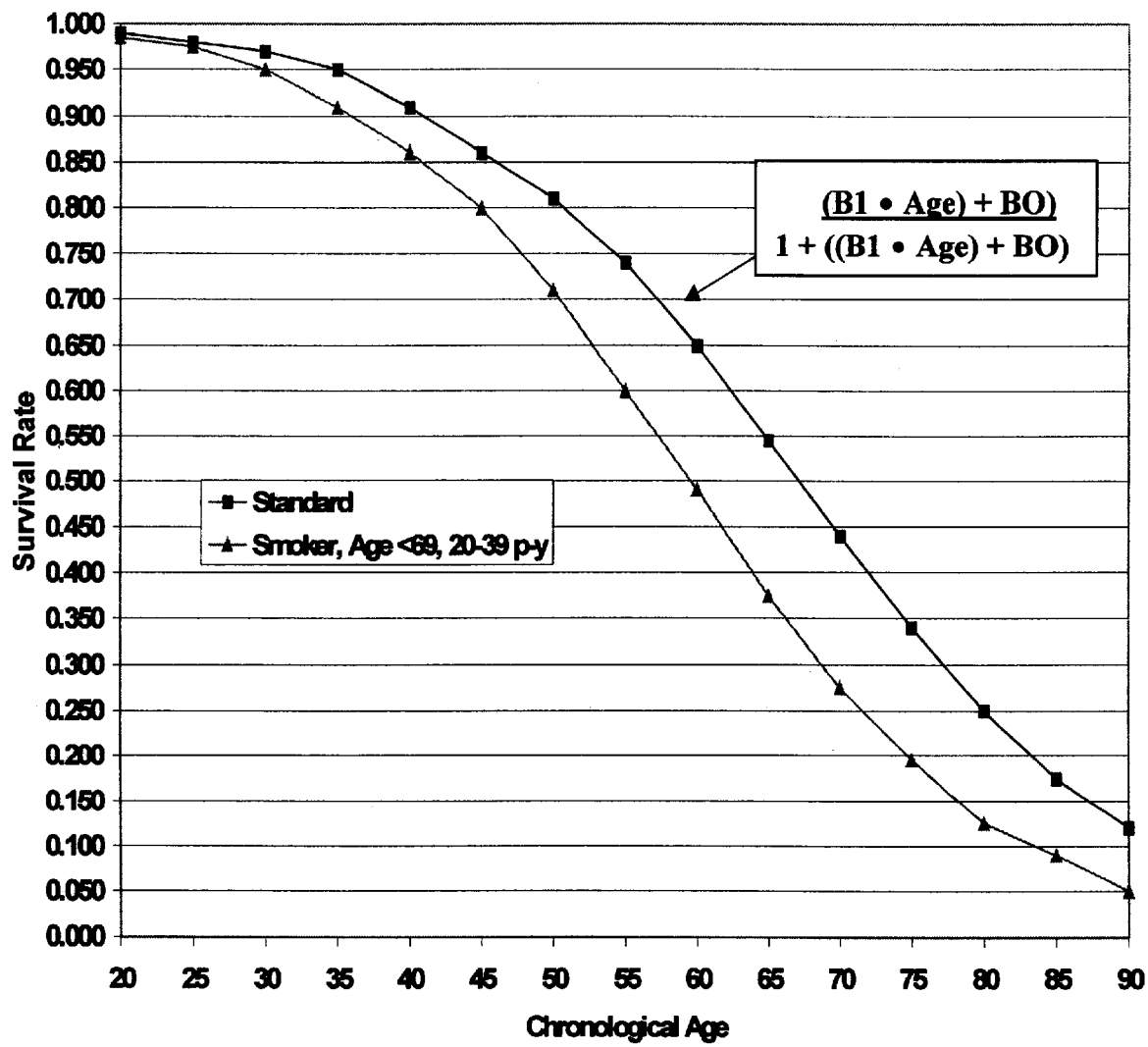
FIG. 10 exemplifies final curve model points (attributes) for two individuals.

FIG. 10 exemplifies final curve model points (attribute) for a smoker, age 69, who has smoked for 20–39 pack years (packs per year) and for a standard individual.

The standard population curve properties for Beta1 ($\beta_{1S}$) and Beta0 ($\beta_{0S}$) are thus determined as follows:

$$\beta_{1S} = \frac{\ln\left(\frac{ASR_{SL}}{1-ASR_{SL}}\right) - \ln\left(\frac{ASR_{SU}}{1-ASR_{SU}}\right)}{LAL - UAL}$$

$$\beta_{0S} = \ln\left(\frac{ASR_{SL}}{1-ASR_{SL}}\right) - (LAL * \beta_{1S})$$

Figure 11:
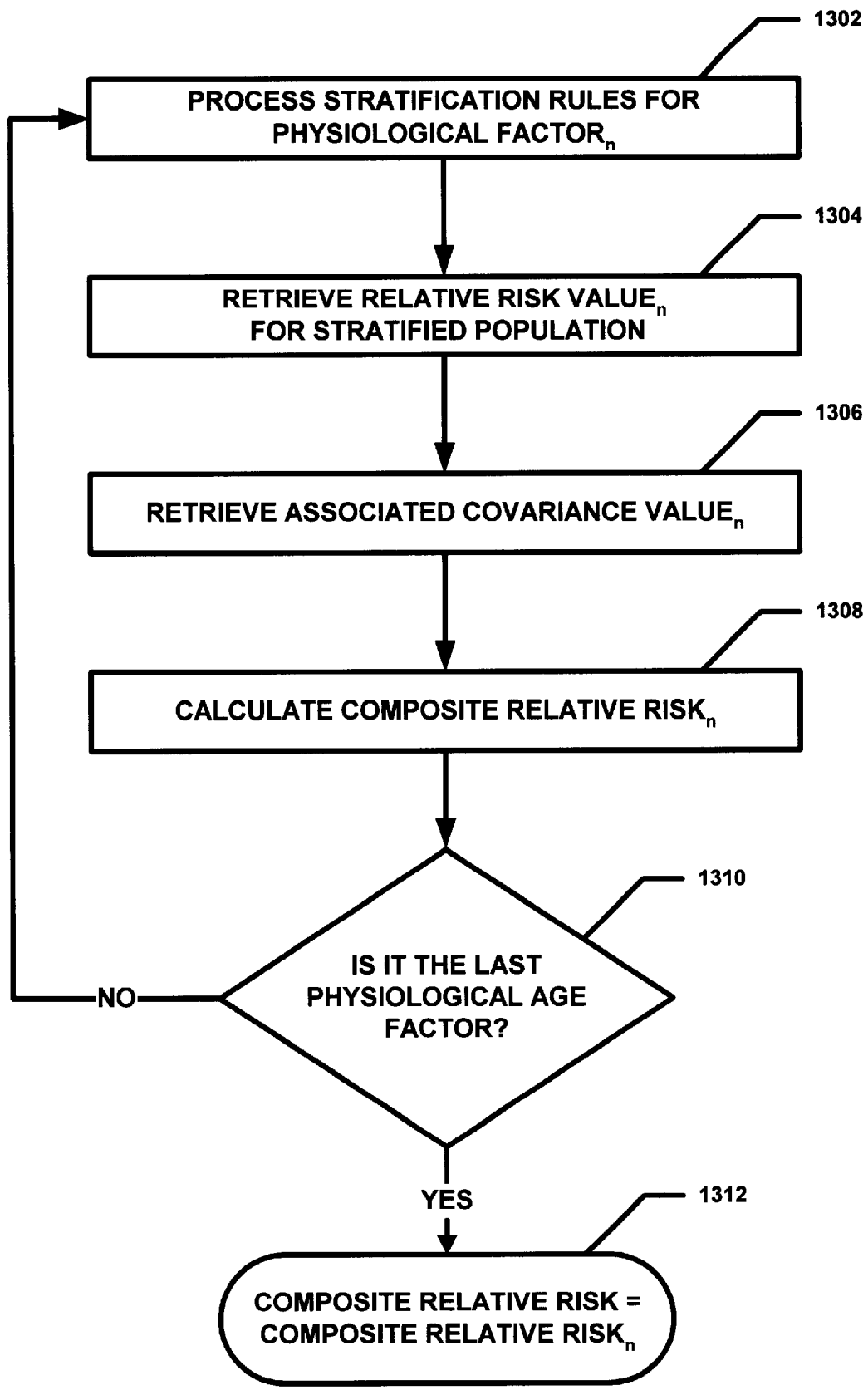
FIG. 11 sets forth the steps required in determining composite relative risk.

FIG. 11 sets forth the steps required to determine the composite relative risk. This process involves processing the stratification rules for a physiological factor$_n$ 1302, where "n" range is equal to (1, number of the last physiological factor); retrieving the relative risk value for the stratified population relating to the chosen factor 1304; retrieving the associated covariance value 1306; and calculating the composite relative risk 1308.

Covariance is a statistical measurement of how variables or factors affect each other. Most wellness factors covary. The covariance adjustment isolates the independent effect of each wellness factor. The results are then used to adjust the relative risk. Covariance adjustment includes calculating composite cardiovascular relative risk; constructing relative risk range for cancer and cardiovascular disease; calculating composite stress relative risk; and constructing relative risk range for stress. The covariance values are revised as wellness factors, and are added or removed as relative risk values are modified.

Calculating the composite relative risk involves the following considerations:

If relative risk$_n$>1.00=Composite $RR_{(n-1)} * ((RR_n - 1.00) * (1.00 - Covariance_n))$ If relative risk$_n$=1.00=1* Composite $RR_{(n+1)}$ If relative risk$_n$<1.00=Composite $RR_{(n-1)} * ((1.00 - RR_n * ((1.00 - Covariance_n))$ It must then be determined whether the chosen physiological factor was the last to be processed 1310. If the answer is yes, then the composite relative risk determined is equal to the total composite relative risk 1312. If the answer is no 1314, then steps 1302 through 1310 are repeated until all physiological factors have been processed.

EXAMPLE

To calculate composite cancer and cardiovascular risk for a 50 year old male, based on the wellness factors alcohol, aspirin use, blood pressure, cholesterol and HDL, heart rate (assumes 3500 calories per week), lycopene, treadmill, vitamin C, vitamin E, folate, calcium, smoking, carnivores, dietary cholesterol, dietary diversity, dietary fiber, stress and health status, the following steps are performed: (1) abstract the optimal relative risks related to cancer and cardiovascular diseases for a 50 year old male from the pool of studies; (2) estimate the proportion of the optimal relative risk that prevents cancer and cardiovascular diseases; (3) proportion out the effects not related to cancer and cardiovascular diseases using the estimated proportions; (4) grade the quality of studies, recognizing that factors other than the studied factor could influence the mortality probability; (5) adjust the lists of related factors and modify them and (6) derive a secondary proportional adjustment to the relative risks that accounts for the quality of the studies and omission of important related factors. Table Two sets forth an example determination of composite cancer and cardiovascular risks for a 50 year old male taking into account the aforementioned factors.

TABLE 2

| Cancer & Cardiovascular Wellness Factors | Relative Risk | Proportional Adjustment To Isolate Factor's Effect on Cancer & Cardiovascular Caused Mortality | First Relative Risk Adjustment | Proportional Adjustment Based on Study Quality and Modified Related Factors List | Second Relative Risk Adjustment |
|---|---|---|---|---|---|
| Alcohol | 0.84 | 100% | 0.84 | 100% | 0.84 |
| Aspirin Use | 0.96 | 100% | 0.96 | 100% | 0.96 |
| Blood Pressure | 0.77 | 100% | 0.77 | 100% | 0.77 |
| Cholesterol & HDL | 0.78 | 100% | 0.78 | 90% | 0.80 |
| Heart Rate (assumes 3500 cals/wk) | 0.95 | 100% | 0.95 | 100% | 0.95 |
| Lycopene | 1.00 | 100% | 1.00 | 50% | 1.00 |
| Treadmill | 0.70 | 70% | 0.70 | 90% | 0.73 |
| Vitamin C | 0.77 | 90% | 0.79 | 100% | 0.79 |
| Vitamin E | 0.77 | 90% | 0.79 | 100% | 0.79 |
| Folate | 0.77 | 90% | 0.79 | 100% | 0.79 |
| Calcium | 1.00 | 0% | 0.00 | 100% | 0.79 |
| Smoking | 0.77 | 100% | 0.80 | 90% | 0.82 |
| Carnivores | 0.70 | 100% | 0.70 | 80% | 0.61 |
| Dietary Cholesterol | 0.82 | 100% | 0.82 | 80% | 0 61 |
| Dietary Diversity | 0.99 | 100% | 0.99 | 80% | 0.61 |

TABLE 2-continued

| Cancer & Cardiovascular Wellness Factors | Relative Risk | Proportional Adjustment To Isolate Factor's Effect on Cancer & Cardiovascular Caused Mortality | First Relative Risk Adjustment | Proportional Adjustment Based on Study Quality and Modified Related Factors List | Second Relative Risk Adjustment |
|---|---|---|---|---|---|
| Dietary Fiber | 0.90 | 100% | 0.90 | 80% | 0.61 |
| Stress | 0.27 | 80% | 0.41 | 60% | 0.65 |
| Health Status | 0.59 | 80% | 0.67 | 60 | 0.80 |

The relative risk mortality for a 50 year old male having the aforementioned wellness factors is 0.07. Therefore, the composite cancer and cardiovascular relative risk is 0.07, adjusted for effect on cancer and cardiovascular diseases, study quality rating and modified related factors list.

Figure 12:
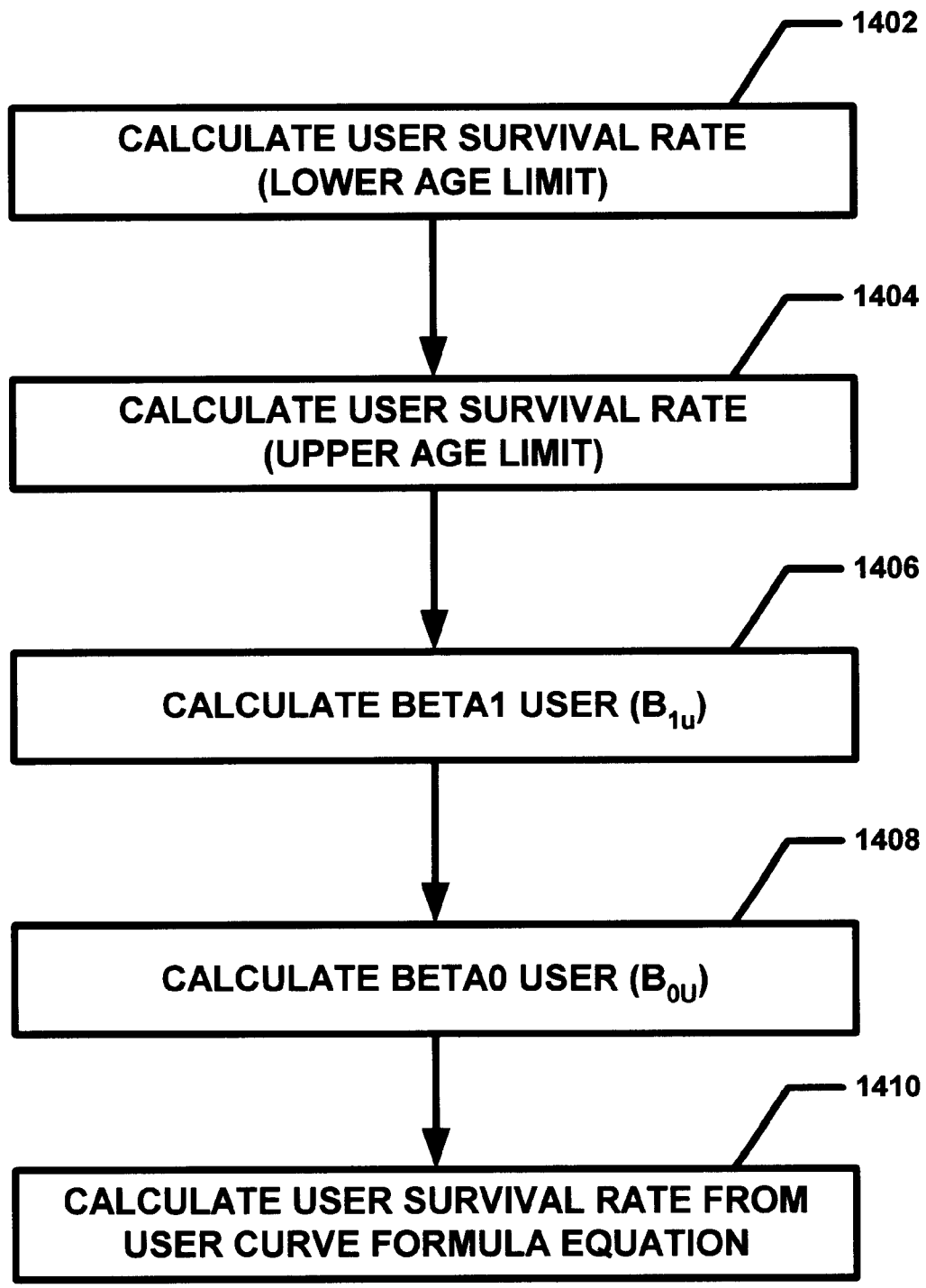
FIG. 12 sets forth the steps involved in calculating the survival rate for a user's composite relative risk.

FIG. 12 sets forth steps involved in calculating the survival rate for a user's composite relative risk. This involves calculating the lower age limit of user survival rate 1402, calculating the upper age limit of user survival rate 1404, calculating Beta1 user ($\beta_{1u}$) 1406, calculating Beta0 user ($\beta_{0u}$) 1408, and calculating the user survival rate from user curve formula equation 1410.

Where U equals User, L equals Lower, S equals standard, and U' equals upper, the user absolute survival rate for the lower age limit is: $(ASR_{UL}) = ASR_{SL}^{Composite\ Relative\ Risk}$ and the user absolute survival rate for the upper age limit is: $(ASR^{UU'}) = ASR_{SU'}^{Composite\ Relative\ Risk}$ The user survival curve properties are determined as follows:

$$\beta_{1U} = \frac{\ln\left(\frac{ASR_{UL}}{1-ASR_{UL}}\right) - \ln\left(\frac{ASR_{UU'}}{1-ASR_{UU'}}\right)}{UAL - LAL}$$

$$\beta_{0U} = \ln\left(\frac{ASR_{UL}}{1-ASR_{UL}}\right) - (LAL * \beta_{1U})$$

The current user survival rate is determined from the user curve formula equation as follows:

$$ASRUC = \frac{e^{\beta 0U + (\beta 1U * Chronological\ Age)}}{1 + e^{\beta 0U + (\beta 1U * Chronological\ Age)}}$$

The physiological age is calculated by determining f(x), f'(x) and then using a recursive calculation process described below.

F(x) is determined by:

$$\frac{EXP(\beta 0(standard) + (\beta 1(standard) * Physiological\ age\ iterative\ value))}{1 + EXP(\beta 0(standard) + (\beta 1(standard) * Physiological\ age\ iterative\ value))} - Attribute\ survival\ rate\ (constant)$$

F(x) can also be expressed by:

$$\frac{Non\text{-}linear\ survival\ proportion\ value + Survival\ proportion\ value\ unadjusted}{1 + Non\text{-}linear\ survival\ proportion\ value + Survival\ proportion\ value\ unadjusted}$$

where the non-linear survival proportion value is equal to the exponential of the survival proportion value adjusted; the survival proportion adjusted is equal to Beta0(standard) plus the survival proportion value unadjusted; and the survival proportion unadjusted is equal to Beta1(standard) times the physiological age iterative value, and the first physiological age value is the chronologic age. The standard survival rate is thus equal to the non-linear survival proportion value divided by the non-linear survival proportion value plus one. Therefore, the survival standard and attribute rate difference is equal to the standard survival rate minus the attribute survival rate, where the attribute survival rate value is obtained from the current five year range. Thus, f(x) is equal to the difference between the standard and attribute survival rate.

F'(x) is determined by:

$$\frac{B1(standard) * (EXP(B0(standard) + (B1(standard) * Physiological\ age\ iterative\ value)))}{(1 + EXP(B0(standard) + (B1(standard) * Physiological\ age\ iterative\ value)))^2}$$

F'(x) is thus limited to the slope of f(x); that is f'(x) will approach a limit as attribute and standard survival rate differences become smaller.

Figure 13:
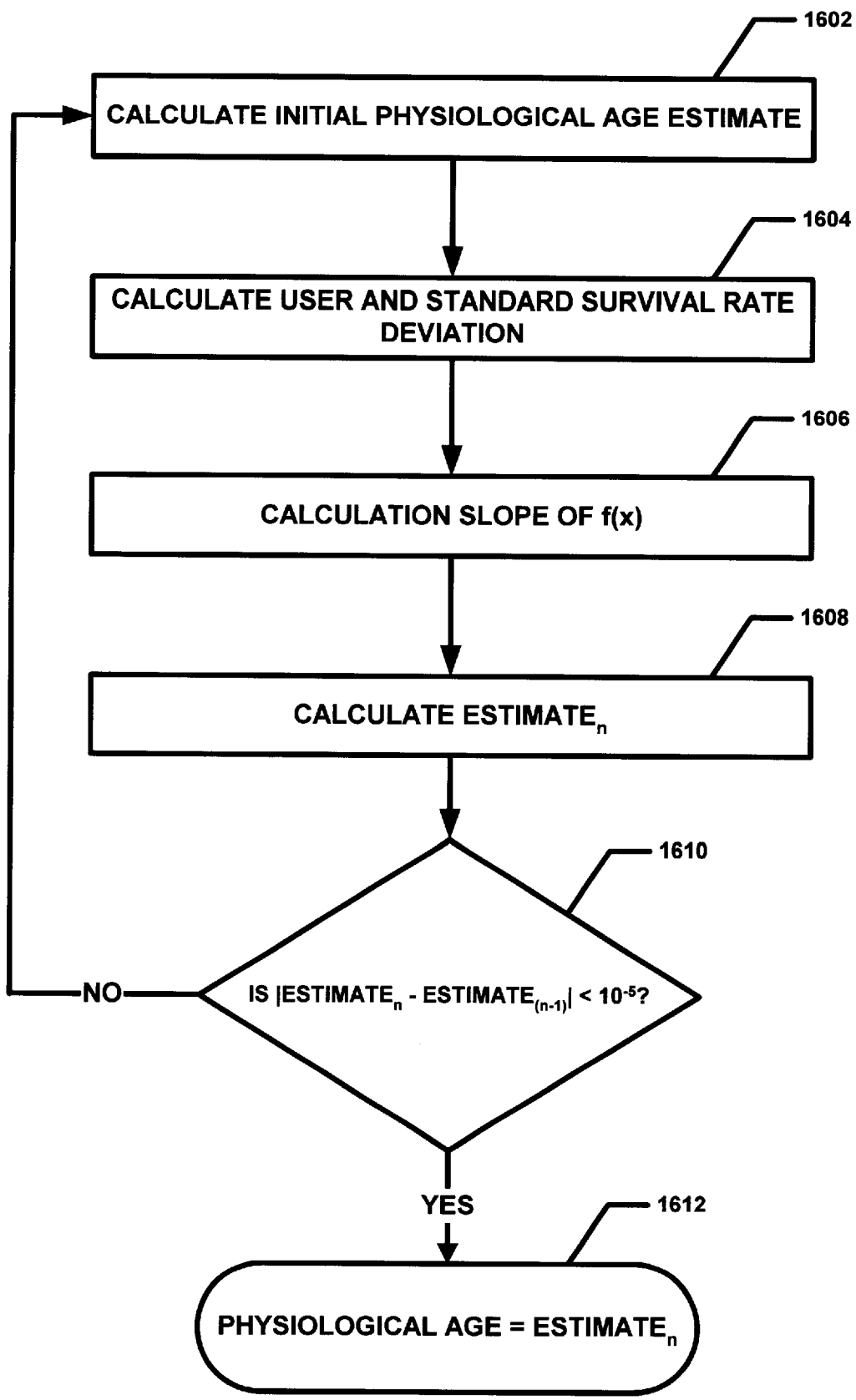
FIG. 13 depicts the process of determining physiological age through recursive calculations.

FIG. 13 depicts the process of determining physiological age through recursive calculations. This involves calculating an initial physiological age estimate 1602, calculating user and standard survival rate deviation 1604, calculating the slope of f(x) 1606, calculating estimate$_n$ 1608, and determining whether estimate$_n$ minus estimate$_{(n-1)}$ is less that $10^{-5}$ 1610. If it is less than $10^{-5}$ 1612, then the physiological age is equal to estimate$_n$. If it is not equal to $10^{-5}$ 1614, then steps 1602 through 1610 are repeated.

Figure 14:
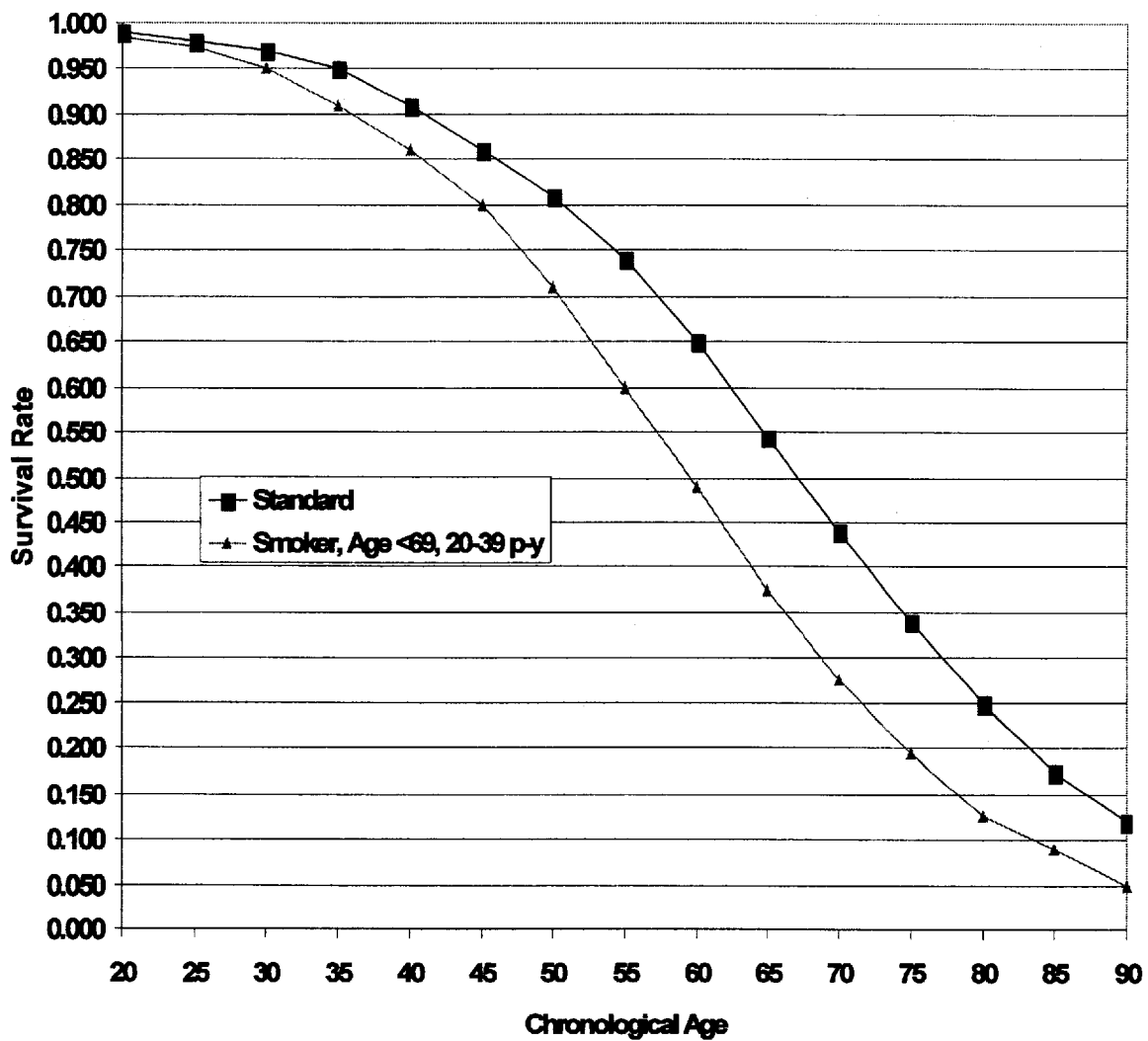
FIG. 14 is a graphical representation depicting the determination of physiological age.

The determination of physiological age is depicted in FIG. 18. The attribute survival rate is known and held constant. F(x) is the standard and attribute survival rate difference. The model successively approximates a standard survival rate for an iterative real number age until the f(x) slope is less than $10^{-6}$. As shown in FIG. 14, a 55 year old smoker who has smoked 20–39 pack years, ( a pack a day for 20 to 39 years) has the same 0.6 probability of ten year survival as a 62.5 year old non-smoker who has never smoked. Therefore, the 55 year old individual who has smoked 20–39 pack years has a physiological age of 62.5 years.

FIG. 15 depicts an example of a window informing the user of his or her physiological age.

Figure 16:
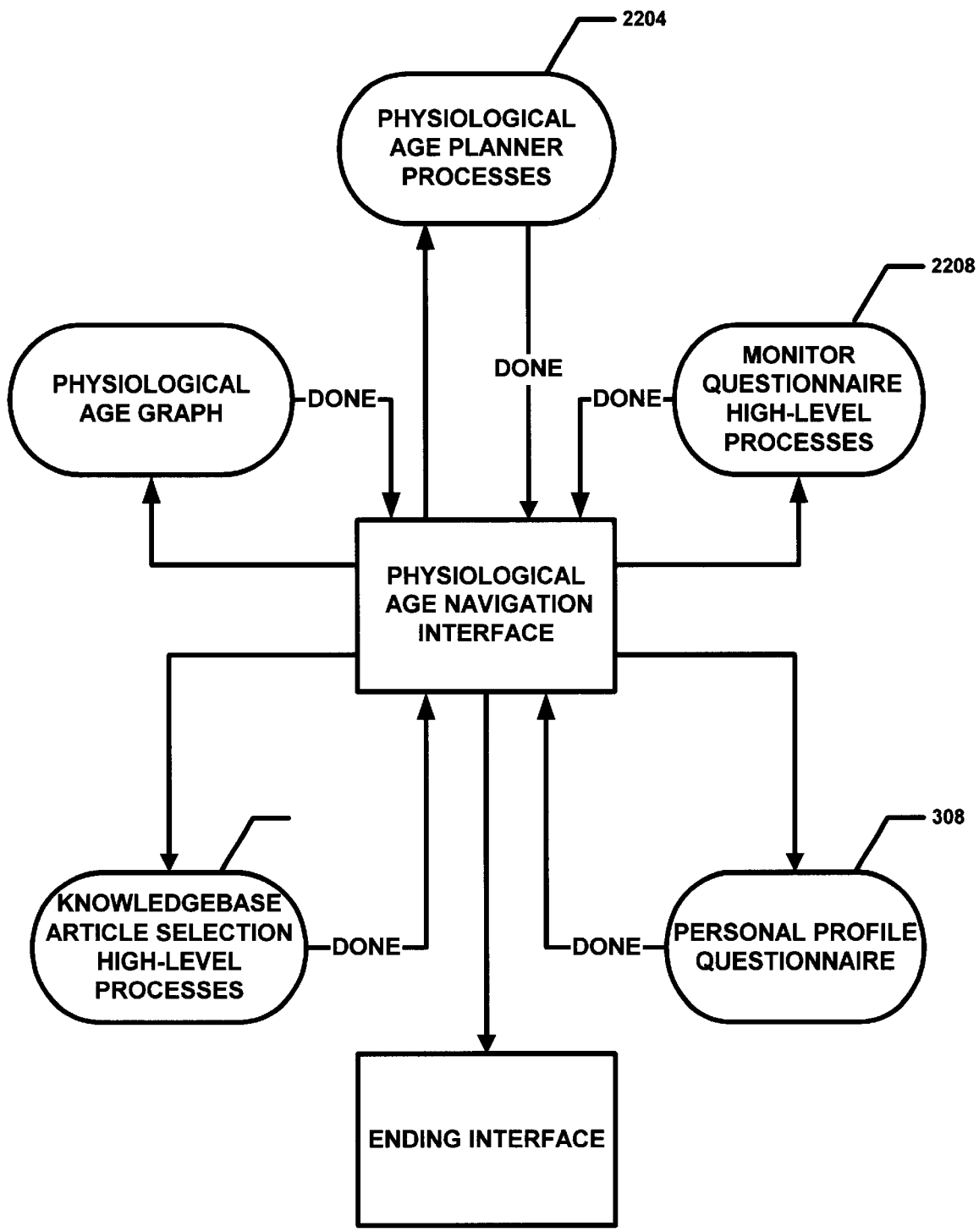
FIG. 16 depicts options available to the user upon entering physiological age navigation interface.

FIG. 16 depicts options available to the user upon entering physiological age navigation interface 310 as depicted in FIG. 3. From this interface, the user can choose to modify plan 2202 by proceeding to physiological age planner processes 2204; enter physiological age planner performance data 2206 by proceeding to monitor questionnaire mode 2208; update their personal profile questionnaire 2210 by proceeding to personal profile questionnaire 308; quit program 2212 by proceeding to physiological age ending interface 2214; view knowledge-based articles 2216 by proceeding to knowledge-based article selection high-level processes 2218; and view the physiological age graph 2220 by proceeding to physiological age graph 312.

Figure 17:
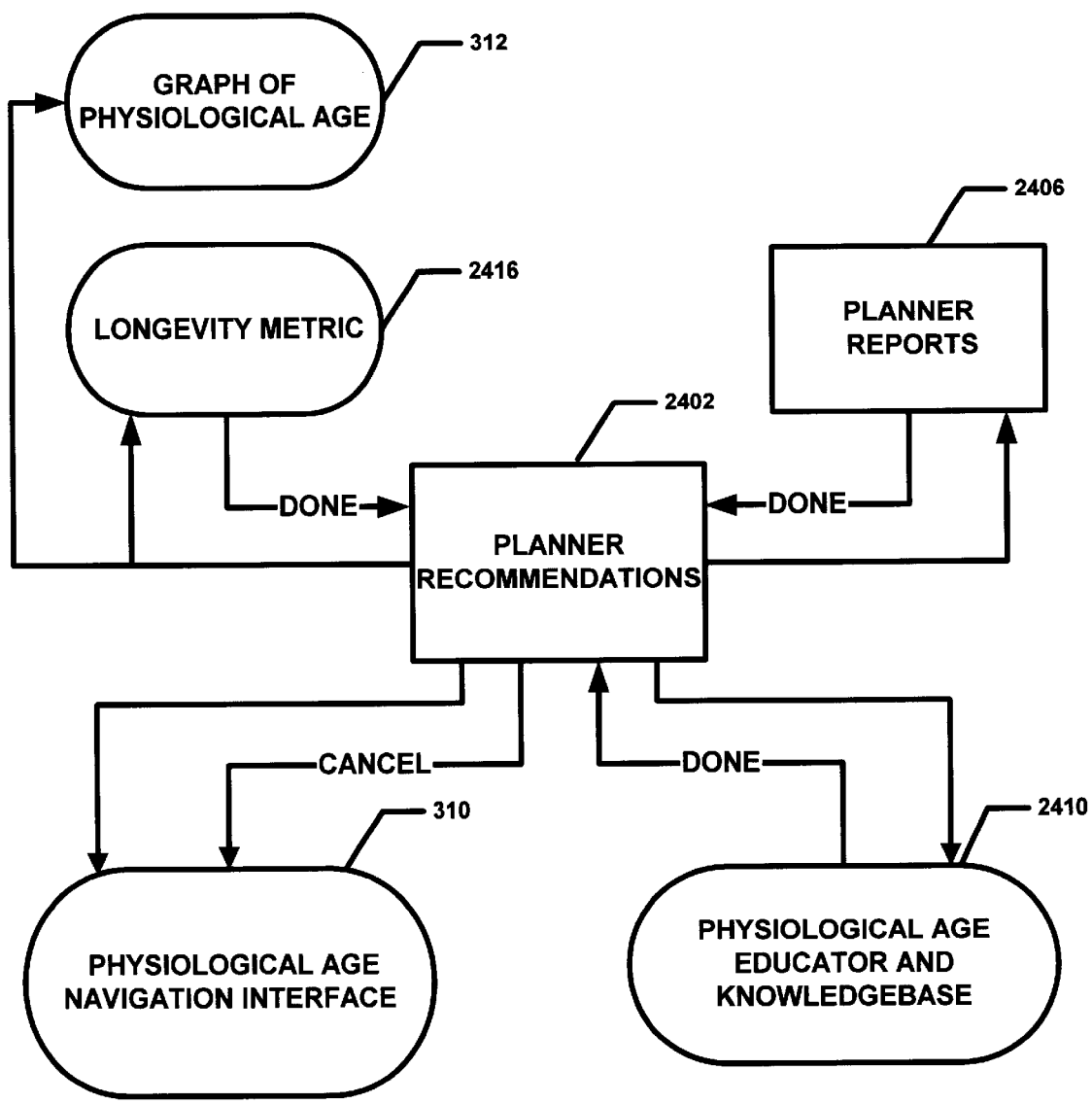
FIG. 17 further depicts the physiological age planner.
Figure 17A:
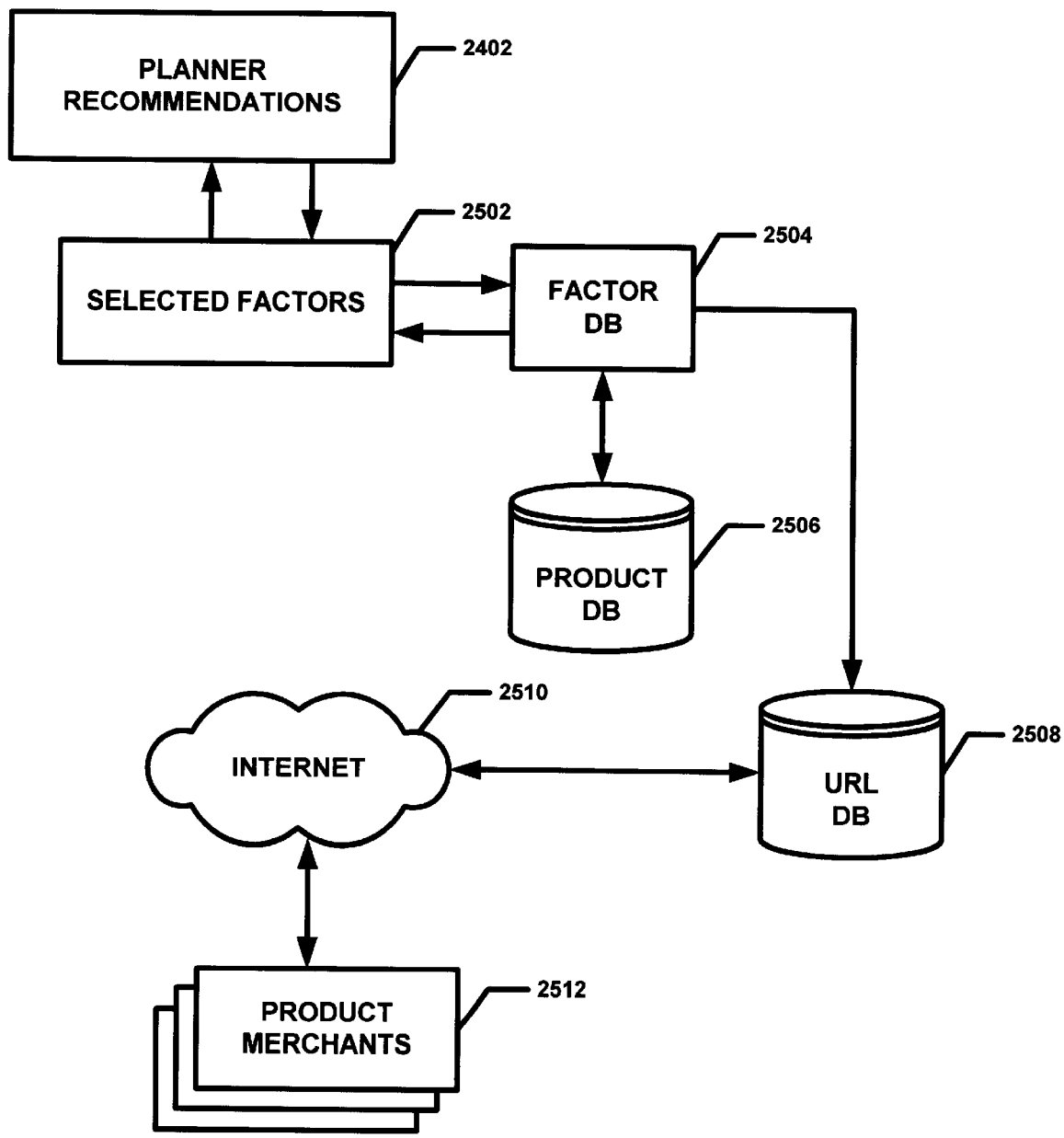
FIG. 17A illustrates the association of products with planner recommendations.

FIG. 17 further depicts the physiological age planner. Upon entering planner recommendations 2402, the user can view and/or select varying planner recommendations. After obtaining this information, the user can choose from several options. The user can view or print the planner reports 2404 by proceeding to planner reports 2406; view the knowledge base 2408 by proceeding to physiological age educator 2410; save the plan 2412 by proceeding to physiological age navigation interface 310 or view the expected physiological age effect of the chosen planner selection 2414 by proceeding to the longevity metric 2416 and graph of physiological age 312.

Referring to FIG. 17 A, the association of products with planner recommendations is shown. As noted earlier, planner recommendations 2402 arrives at recommendations for a given user based upon physiological age graphs, the system knowledge base, and other processes noted above. The planner recommendations create tables with selected recommendations noted in FIGS. 18–21 (further explain below). However, whether an individual user adopts a particular planner recommendation depends in part upon how the recommendation is implemented. For example, a particular individual may be more inclined to take a vitamin supplement than to run ten miles per day. Thus the planner recommendations result in a number of selected factors 2502 from which the user can select. The selected factors are further linked to a factor database 2504. This factor database comprises information on products that can be purchased by a user and which directly affect the factor in question.

For example, if the planner recommendations module 2402 recommends taking 250 mg of vitamin C three times per day, the factor database would present to the user commercial sources of vitamin C in 250 mg tablet sizes. Similarly, if the recommendation is to take folate, the factor database would provide information to the user regarding the sources of folate.

Thus the factor database provides references to the user regarding sources for products that would assist the user in implementing the recommendations from the planner recommendations module 2402. These product recommendations occur in at least two fashions: first, the system of the present invention can comprise a product database 2506 which contains specific advertisements and pricing for products of merchants and service providers. When a user is provided with a factor that can reduce his physiological age, the user can simply review the factor, click on a portion of the screen relating to products associated with that factor, and be provided with product information from the product database 2506.

Alternatively, in the event that a user selects a particular factor to evaluate, the factor database will also contain a universal resource locator (URL) database 2508. This database would comprise Internet addresses for merchants that provide products associated with the factor being evaluated. The user could thus click on the factor noted in the factor database 2504, be taken to the appropriate URL address in the URL database 2508. Upon clicking on the Internet address, the user's browser would be launched and the user would be taken to the product or merchant database 2512 over the Internet 2510. In this fashion, the present invention either contains product information that can be directly provided to the user, or alternatively, the user could be taken directly to the Internet to the website of those merchants selling products that would assist the user in implementing the selected factors from the planning recommendations module 2502.

FIGS. 18, and 19 show examples of physiological age planning windows, without selected plan items, such as would be seen by the user upon entering planner recommendations 2402. As can be seen as well in the Wellness Planner, there is an area of the user interface with the heading "Products." Underneath this heading are a series of areas designated in FIG. 18 29 and 19 as circles, however, this is not meant as a limitation. These are areas where the user clicks to designate that the user is interested in obtaining information concerning the specific product that would assist the user in dealing with the recommendations listed. For example, referring to FIG. 18, a user who is interested in cigarette smoking, but does not know the various products that are available to assist in this regard, can click on the "Products" designator associated with that recommendation and be lead to the products stored in the product database 2506 that deal with products to assist smokers in quitting smoking. Alternatively, that product designator would also lead to a listing of websites in the URL database 2508 which, when clicked upon, will launch the user's web browser and take the user to the product merchant's site 2512 over the Internet 2510. In this fashion, a user of the present invention can see what assistance is available with each recommendation, and therefore make an informed determination of whether the user can take the action required to mitigate the particular factor in question, whether it be cigarette smoking, cholesterol level, exercise issues, and the like. FIGS. 20, and 21 show examples of physiological age planning windows, with selected plan items. Also noted in FIGS. 20 and 21 are the product designator areas associated with each recommendation. As can be seen in FIGS. 20 and 21, a product designation area is associated with each recommendation.

FIGS. 22, 23, 24 and 25 show examples of planner reports such as would be presented to the user upon proceeding to planner reports 2206. Referring to FIG. 22, a summary of the Wellness Plan created by the planner reports module 2206 is shown. This figure shows the choices of recommendations selected by the user, in this case to stop smoking, to reduce cholesterol, to reduce blood pressure, to take vitamin C, to take folate, and to take vitamin E. The figure further contains a block which the user can check to again see a summary of the products that are associated with the selected recommendations. Checking this block would give a further report to the user listing the contact information for those merchants that sell products and services to assist the user in the recommendations that are selected. For example, sources of folate would be identified as to the merchant, the URL associated with the merchant's website, an 800 number to contact for sales information, and other information that would assist the user in obtaining the products to support the user's choice of recommendations for lowering the user's physiological age.

Depending upon the product or service desired, these products could be endorsed by the system manager of the present invention for a fee, which fee would be paid to the operator of the present invention once it has been determined by the system operator that the products noted can truly meet the needs of users making specific choices of recommendations.

FIGS. 26, 27, 28 and 29 show examples of educator windows such as would be presented to the user upon proceeding to physiological age educator 2210.

Figure 30:
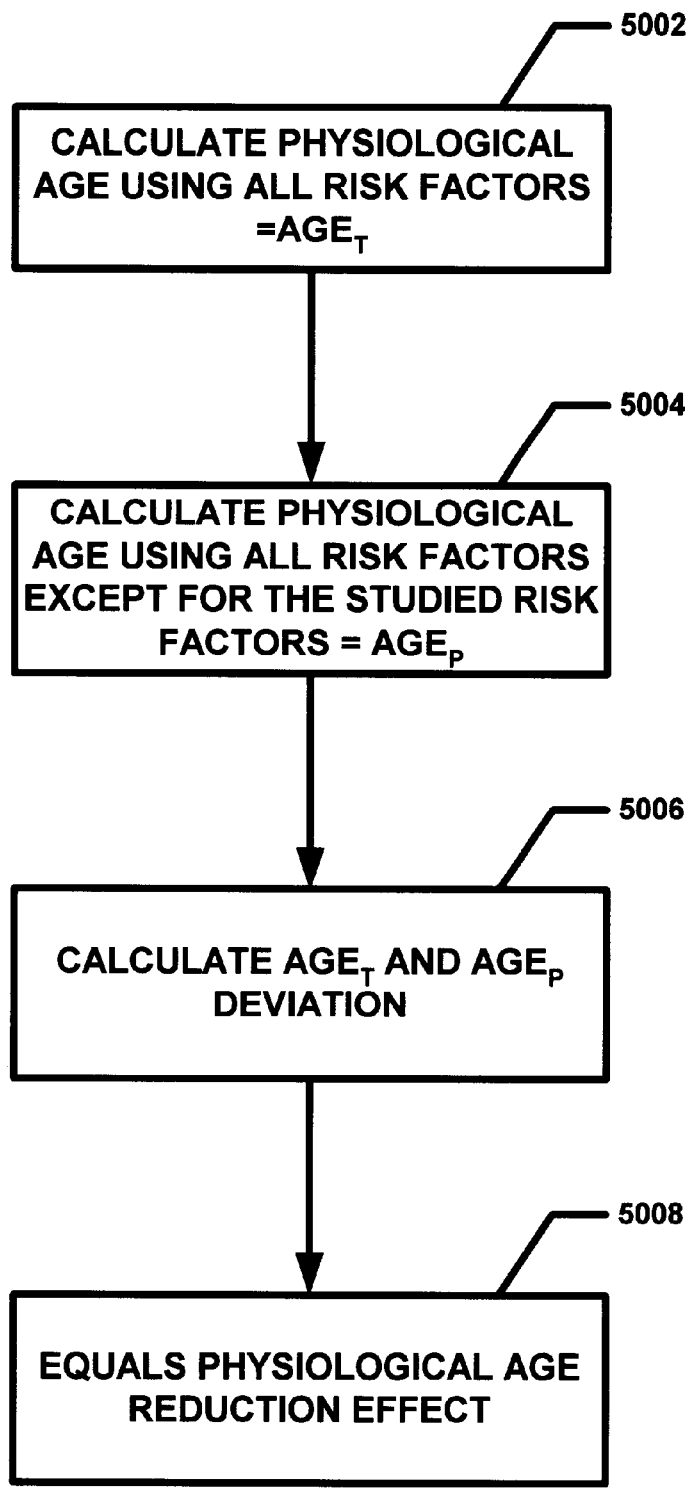
FIG. 30 shows an example of the physiological age factor effect calculation process.

FIG. 30 depicts the process of determining the effect of a planner selection upon the user's physiological age. This requires calculating the user's physiological age using all risk factors 5002, calculating the physiological age using all risk factors except for the studied risk factor 5004, and determining the deviation between these two results 5006. The deviation is equal to the physiological age reduction effect 5008.

The user is thus presented with a list of planner options that have been chosen by the system based upon input by the user. Using the list, the user can select one or more of the options to form a wellness plan. The user can then determine the physiological effect of implementing the chosen wellness plan. This process can be repeated such that the user can evaluate the effects of various wellness plans, and then decide upon their preferred plan. This allows a user to evaluate the benefits of varying combinations of planner options. In a preferred embodiment, the results that could be obtained by implementing a particular wellness plan are presented for a short term interval (such as three months) and a long term interval (such as three years).

Once a wellness plan has been chosen, the present invention allows the user to monitor their progress in improving wellness. In addition, the user can continue to use the program to change and/or augment their wellness plan.

Although the present invention has been described in detail for purpose of illustration, it is understood that such detail is solely for that purpose, and variations can be made therein by those skilled in the art without departing from the spirit and scope of the invention. The present invention is defined by the following claims.

What is claimed is:

1. An interactive wellness system comprising:
   means for collecting information relating to a user's wellness factors;
   means responsive to the user's wellness factor information collecting means for determining the user's physiological age;
   means responsive to the user's wellness factor information collecting means for providing the user with wellness program options for improving the user's wellness;
   means for allowing the user to select from the wellness program options to form a wellness plan; and
   means for allowing the user to determine the effects the selected wellness plan has on the user's physiological age;
   means for identifying products associated with the user-selected options.

2. An interactive wellness system according to claim 1, wherein the wellness program options are chosen in response to the information related to a user's wellness factors.

3. An interactive wellness system according to claim 1, further comprising:
   means for allowing the user to select a preferred wellness plan.

4. An interactive wellness system according to claim 3, further comprising:
   means responsive to the preferred wellness plan selection means for presenting a description of the chosen wellness plan.

5. An interactive wellness system according to claim 4, further comprising:
   means responsive to the description presentation means for providing the user with further information related to various aspects of the chosen wellness plan.

6. An interactive wellness system according to claim 1, wherein information related to the user's wellness factors comprises information related to the user's life style, habits, environment, and health, medical and genetic history.

7. An interactive wellness system according to claim 1, further comprising:
   means for determination of the user's changing physiological age.

8. An interactive wellness system according to claim 3, wherein the results of implementing a chosen wellness plan are presented to the user.

9. An interactive wellness system according to claim 8, wherein the results of implementing a chosen wellness plan over a short term and the results of implementing a chosen wellness plan over a long term are presented to the user.

10. An interactive wellness system according to claim 8, wherein the potential results of implementing a chosen wellness plan for a three month period and a three year period are presented to the user.

11. An interactive wellness system according to claim 8, wherein the results presented are in the form of physiological age.

12. An interactive wellness system according to claim 1, wherein the user's wellness factor information can be updated at a time after initial collection of the user's wellness factor information.

13. An interactive wellness system according to claim 3, wherein the user can select a new preferred wellness plan after the initial selection of the preferred wellness plan.

14. An interactive wellness system according to claim 1, wherein the means for collecting wellness factor information comprises decision nodes that allow the user to skip irrelevant or unnecessary questions.

15. An interactive wellness system according to claim 1, further comprising:
   is means for determining a composite relative risk responsive to the user's collected wellness factor information.

16. An interactive wellness system according to claim 1, wherein means for collecting information related to a user's wellness factors further comprises:
   a questionnaire, wherein the questionnaire elicits information pertaining to a series of wellness factors.

17. An interactive wellness system according to claim 16, wherein a user inputs wellness factor data in response to the questionnaire.

18. An interactive wellness system according to claim 17, wherein the wellness factor data is stored in a data base table.

19. An interactive wellness system according to claim 18, wherein the wellness factor data is manipulated into transformed data.

20. An interactive wellness system according to claim 19, wherein the transformed data is stored in a database table for transformed data.

21. An interactive wellness system according to claim 20, wherein a means for determining the user's physiological age further comprises:

means for processing each of a user's wellness factors according to stratification rules;

means responsive to the stratification rule processing for determining a relative risk value for each of the user's wellness factors;

means for adjusting the wellness factor relative risk results for covariance; and means responsive to the user's wellness factor relative risk calculation for determining the user's equivalent survival rate and physiological age.

22. A method of creating and selecting a wellness program comprising:

inputting data relating to a user's wellness factors;

storing the user's wellness factor data input data;

manipulating the user's wellness factor data into transformed data;

storing the transformed data;

manipulating the transformed data to determine the user's physiological age;

presenting physiological age to the user;

determining wellness program options based upon the user's wellness factor data and the transformed data;

presenting the wellness program options to the user;

selecting wellness program options by the user to form a wellness plan; and calculating the physiological age change that occurs if the user adopts the selected wellness plan; and identifying for the user products associated with selected wellness plan options.

23. A method of creating and selecting a wellness program according to claim 22, further comprising allowing the user to select and appraise the potential effects of various wellness plans.

24. A method of creating and selecting a wellness program according to claim 23, further comprising the user choosing a preferred wellness plan.

25. A method of creating and selecting a wellness program according to claim 24, further comprising presenting the preferred wellness plan to the user.

26. A method of creating and selecting a wellness program according to claim 25, further comprising providing the user with further information relating to various aspects of the preferred wellness plan.

27. A method of creating and selecting a wellness program according to claim 22, wherein data relating to the user's wellness factors comprises information relating to a user's life style, habits, environment, and health, medical, and genetic history.

28. A method of creating and selecting a wellness program according to claim 22, further comprising determining the change in a user's physiological age.

29. A method of creating and selecting a wellness program according to claim 24, further comprising presenting the physiological age effect of implementing a chosen wellness plan to the user.

30. A method of creating and selecting a wellness program according to claim 29, wherein the results of implementing a chosen wellness plan over the short term and the results of implementing a chosen wellness plan over the long term are presented to the user.

31. A method of creating and selecting a wellness program according to claim 29, wherein the results of implementing a chosen wellness plan for a three month and a three year period are presented to the user.

32. A method of creating and selecting a wellness program according to claim 29, wherein the results presented are in the form of physiological age.

33. A method of creating and selecting a wellness program according to claim 22, further comprising:

updating information relating to the user's wellness factors at a time after initial inputting of the user's wellness factor data.

34. A method of creating and selecting a wellness program according to claim 23, further comprising:

selecting a new preferred wellness plan after initial selection of the preferred wellness plan.

35. A method of creating and selecting a wellness program according to claim 22 further comprising the automatic skipping of irrelevant or unnecessary questions.

36. A method of creating and selecting a wellness program according to claim 22 further comprising determining a composite relative risk based upon the user's wellness factor data.

37. A method of creating and selecting a wellness program according to claim 22 wherein inputting data relating to the user's wellness factors results from the user responding to a questionnaire.

38. A method of creating and selecting a wellness program according to claim 22 wherein the determination of the user's physiological age further comprises:

processing the user's wellness factors according to stratification rules;

determining a relative risk vale for each of the user's wellness factors according to the stratification rules;

adjusting the wellness factor relative risk values for covariance; and determining the user's equivalent survival rate and physiological age.

39. The system of claim 1 wherein the products identified are products for which advertising fees are paid.

40. The system of claim 1 wherein the products identified are products for which no advertising fees are paid.

41. The method of claim 22 further comprising paying for an endorsement of the products identified to the user.

42. The method of claim 22 further comprising identifying products to the user without requiring endorsement fees to be paid.

* * * * *